(12) United States Patent
Zankel et al.

(10) Patent No.: US 9,951,013 B2
(45) Date of Patent: Apr. 24, 2018

(54) FUCOSIDASE INHIBITORS

(71) Applicant: HORIZON ORPHAN LLC, Lake Forest, IL (US)

(72) Inventors: Todd C. Zankel, San Francisco, CA (US); Sara Louise Isbell, Novato, CA (US); Amanda Anne Ko, San Rafael, CA (US)

(73) Assignee: Horizon Orphan LLC, Lake Forest, IL (US)

(*) Notice: Subject to any disclaimer, the term of this patent is extended or adjusted under 35 U.S.C. 154(b) by 0 days.

(21) Appl. No.: 15/225,188

(22) Filed: Aug. 1, 2016

(65) Prior Publication Data
US 2017/0029376 A1 Feb. 2, 2017

Related U.S. Application Data

(60) Provisional application No. 62/199,194, filed on Jul. 30, 2015.

(51) Int. Cl.
| | |
|---|---|
| *C07D 211/46* | (2006.01) |
| *C07D 211/74* | (2006.01) |
| *A61K 31/445* | (2006.01) |
| *A61K 9/00* | (2006.01) |
| *A61K 45/06* | (2006.01) |

(52) U.S. Cl.
CPC .......... *C07D 211/46* (2013.01); *A61K 9/0019* (2013.01); *A61K 31/445* (2013.01); *A61K 45/06* (2013.01); *C07D 211/74* (2013.01)

(58) Field of Classification Search
None
See application file for complete search history.

(56) References Cited

U.S. PATENT DOCUMENTS

| | | | |
|---|---|---|---|
| 4,394,448 | A | 7/1983 | Szoka, Jr. et al. |
| 5,017,704 | A | 5/1991 | Fleet et al. |
| 5,096,909 | A | 3/1992 | Fleet et al. |
| 5,100,797 | A | 3/1992 | Fleet et al. |
| 5,153,325 | A | 10/1992 | Fleet et al. |
| 5,186,941 | A | 2/1993 | Callahan et al. |
| 5,240,707 | A | 8/1993 | Farr et al. |
| 5,382,709 | A | 1/1995 | Farr et al. |
| 5,962,012 | A | 10/1999 | Lin et al. |
| 6,261,595 | B1 | 7/2001 | Stanley et al. |
| 2011/0189084 | A1 | 8/2011 | Zankel |

FOREIGN PATENT DOCUMENTS

WO   WO-2014/032184 A1   3/2014

OTHER PUBLICATIONS

Movassaghi, M. et al. Total Synthesis and Absolute Stereochemical Assignment of (+)- and (−)-Galbulimima Alkaloid 13. JACS Communications. 2006, vol. 128, p. 8126.*
Movassaghi, M. et al. Total Synthesis and Absolute Stereochemical Assignment of (+)- and (−)-Galbulimima Alkaloid 13—Supplementary Information. JACS Communications. 2006, vol. 128, p. S54.*
Burger, AM. Preclinical Screening for New Anticancer Agents. Springer. 2014, p. 23.*
Aihara et al., The selective Aurora B kinase inhibitor AZD1152 as a novel treatment for hepatocellular carcinoma, J. Hepatol., 52(1):63-71 (2010).
Armengol et al., Orthotopic implantation of human hepatocellular carcinoma in mice: analysis of tumor progression and establishment of the BCLC-9 cell line, Clin. Cancer Res., 10(6):2150-7 (2004).
Bause et al., N-methyl-N-(5-carboxypentyl)-1-deoxynojirimycin, a new affinity ligand for the purification of trimming glucosidase I, FEBS Lett., 278(2):167-70 (1991).
Block et al., Use of targeted glycoproteomics to identify serum glycoproteins that correlate with liver cancer in woodchucks and humans, Proc. Natl. Acad. Sci. USA, 102(3):779-84 (2005).
Chan et al., Inhibition of P-glycoprotein expression and reversal of drug resistance of human hepatoma HepG2 cells by multidrug resistance gene (mdr1) antisense RNA, Life Sci., 67(17):2117-24 (2000).
Comunale et al., Identification and development of fucosylated glycoproteins as biomarkers of primary hepatocellular carcinoma, J. Proteome Res., 8(2):595-602 (2009).
Danesi et al., Pharmacokinetic-pharmacodynamic relationships of the anthracycline anticancer drugs, Clin. Pharmacokinet., 41(6):431-44 (2002).
Genbank Accession No. NP_000138, tissue alpha-L-fucosidase precursor [*Homo sapiens*], Oct. 6, 2016.
Giardina et al., Serum alpha-L-fucosidase activity and early detection of hepatocellular carcinoma: a prospective study of patients with cirrhosis, Cancer, 83(12):2468-74 (1998).
Giardina et al., Serum alpha-L-fucosidase. A useful marker in the diagnosis of hepatocellular carcinoma, Cancer, 70(5):1044-8 (1992).
Hakomori, Tumor-associated carbohydrate antigens defining tumor malignancy: basis for development of anti-cancer vaccines, Adv. Exp. Med. Biol., 491:369-402 (2001).
Hu et al., Genetic alterations in doxorubicin-resistant hepatocellular carcinoma cells: a combined study of spectral karyotyping, positional expression profiling and candidate genes, Int. J. Oncol., 25(5):1357-64 (2004).
Intra et al., Comparative and phylogenetic analysis of alpha-L-fucosidase genes, Gene, 392(1-2):34-46 (2007).
Invitation to Pay Additional Fees and, Where Applicable, Protest Fee, International Application No. PCT/US2016/044607, dated Sep. 29, 2016.
Johnson et al., Molecular defect in processing a-fucosidase in fucosidosis, Biochem. Biophys. Res. Commun., 133:90-7 (1986).
Lammerts van Bueren et al., Structural and thermodynamic analyses of a-L-fucosidase inhibitors, Chembiochem., 11(14):1971-4 (2010).
Lau et al., Transarterial chemoembolization for hepatocellular carcinoma, J. Am. Coll. Surg., 202(1):155-68 (2006).

(Continued)

*Primary Examiner* — Zinna Northington Davis
(74) *Attorney, Agent, or Firm* — Marshall, Gerstein & Borun LLP

(57) ABSTRACT

The present disclosure relates, in general, to compounds useful as inhibitors of fucosidase enzymes, and to methods and compositions for the treatment of tumors or cancers, such as liver disorders and liver tumors (e.g., hepatocellular carcinoma), with a compound as disclosed herein.

24 Claims, 2 Drawing Sheets

(56) References Cited

OTHER PUBLICATIONS

Li et al., New synthetic seven-membered 1-azasugars displaying potent inhibition towards glycosidases and glucosylceramide transferase, Chembiochem., 9(2):253-60 (2008).
Lin et al., Local injection therapy for hepatocellular carcinoma, Hepatobiliary Pancreat. Dis. Int., 5(1):16-21 (2006).
McCormack et al., Miglustat, Drugs, 63(22):2427-34 (2003).
Mehta et al., Fucosylated glycoproteins as markers of liver disease, Dis. Markers., 25(4-5):259-65 (2008).
Michalski et al., Characterization and 400-MHz 1H-NMR analysis of urinary fucosyl glycoasparagines in fucosidosis, Eur. J. Biochem., 201(2):439-58 (1991).
Noda et al., Relationship between elevated FX expression and increased production of GDP-L-fucose, a common donor substrate for fucosylation in human hepatocellular carcinoma and hepatoma cell lines, Cancer Res., 63(19):6282-9 (2003).
Norton et al., N-linked glycosylation of the liver cancer biomarker GP73, J. Cell Biochem., 104(1):136-49 (2008).
Okubo et al., Orthotopic hepatocellular carcinoma model with a controlled and reproducible tumorigenicity, J. Gastroenterol. Hepatol., 22(3):423-8 (2007).
Ong et al., Effective inhibition of xenografts of hepatocellular carcinoma (HepG2) by rapamycin and bevacizumab in an intrahepatic model, Mol. Imaging Biol., 11(5):334-42 (2009).
Plosker et al., Epirubicin. A review of its pharmacodynamic and pharmacokinetic properties, and therapeutic use in cancer chemotherapy, Drugs, 45(5):788-856 (1993).
Ribero et al., Liver resection in the treatment of hepatocellular carcinoma, Expert Rev. Anticancer Ther., 6(4):567-79 (2006).
Tennant et al., Hepatocellular carcinoma in the woodchuck model of hepatitis B virus infection, Gastroenterology, 127(5 Suppl 1):S283-93 (2004).
Tu et al., Development of fucosyltransferase and fucosidase inhibitors, Chem. Soc. Rev., pp. 1-17 (Apr. 15, 2013).
White et al., Further studies on the catalytic mechanism of human liver alpha-L-fucosidase, Biochim. Biophys. Acta, 912(1):132-8 (1987).
Willems et al., Fucosidosis revisited: a review of 77 patients, Am. J. Med. Genet., 38(1):111-31 (1991).
Willems et al., Spectrum of mutations in fucosidosis, Eur. J. Hum. Genet., 7(1):60-7 (1999).
Winchester et al., Inhibition of alpha-L-fucosidase by derivatives of deoxyfuconojirimycin and deoxymannojirimycin, Biochem. J., 265(1):277-82 (1990).
Wu et al., Rapid diversity-oriented synthesis in microtiter plates for in situ screening: discovery of potent and selective alpha-fucosidase inhibitors, Angew. Chem. Int. Ed. Engl., 42(38):4661-4 (2003).
Wu et al., Structural basis of alpha-fucosidase inhibition by iminocyclitols with K(i) values in the micro- to picomolar range, Angew. Chem. Int. Ed. Engl., 49(2):337-40 (2010).
Yao et al., A novel orthotopic tumor model to study growth factors and oncogenes in hepatocarcinogenesis, Clin. Cancer Res., 9(7):2719-26 (2003).
International Search Report and Written Opinion, International Application No. PCT/US2016/044607, dated Dec. 12, 2016.
Wang et al., Synthesis and biological evaluation of glycosidase inhibitors: gem-difluoromethylenated nojirimycin analogues, J. Med. Chem., 49(10):2989-97 (2006).

\* cited by examiner

FUCOSIDASE INHIBITORS

CROSS-REFERENCE TO RELATED APPLICATIONS

This application claims the benefit of U.S. Provisional Application No. 62/199,194, filed Jul. 30, 2015, which is incorporated herein by reference in its entirety.

FIELD OF THE DISCLOSURE

The present disclosure relates, in general, to compounds useful as inhibitors of fucosidase enzymes, and to methods and compositions for the treatment of tumors or cancers, such as liver disorders and liver tumors (e.g., hepatocellular carcinoma), with a compound as disclosed herein.

BACKGROUND

Differences in protein glycosylation have been noted between normal and tumor cells and have been the basis for development of tumor-selective antibodies (Hakomori, S., Adv Exp. Med. Biol., 491:369-402, 2001). It has been observed that hepatocellular carcinoma (HCC) cells significantly and inappropriately fucosylate their glycoproteins relative to normal hepatocytes (Block, T. M. et al., Proc. Natl. Acad. Sci. USA, 102:779-84, 2005; Comunale, M. A. et al., J. Proteome Res. 8:595-602, 2009; Mehta, A. et al., Dis. Markers, 25:259-65, 2008; Noda, K. et al., Cancer Res. 63:6282-9, 2003; Norton, P. A. et al., J. Cell. Biochem. 104:136-49, 2008). A large portion of these glycoproteins end up in the tumor lysosome, where they are degraded. One report has suggested that increased serum levels of lysosomal alpha-L-fucosidase are predictive of HCC, indicating possible upregulation of this enzyme by precancerous hepatocytes in order to accommodate increasing levels of glycoprotein fucosylation in the biosynthetic pathway (Giardina, M. G. et al., Cancer 83:2468-74, 1998). The catalytic mechanism of human liver alpha-L-fucosidase has been investigated (White, W. J. et al., Biochim. Biophys. Acta. 912: 132-8 (1987)).

Inactivation of lysosomal alpha-L-fucosidase (FUCA1), e.g., due to inherited mutations in the gene, results in a lysosomal storage disease (LSD) called fucosidosis (Willems, P. J. et al., Eur. J. Hum. Genet. 7:60-7, 1999; Intra, J. et al., Gene 392:34-46, 2007). Patients presenting with fucosidosis exhibit lysosomal accumulation of undegraded material because they are unable to lysosomally degrade terminal and core-fucosylated oligosaccharides, and rarely survive past their sixth year (Willems, P. J. et al., Am. J. Med. Genet. 38:111-31, 1991).

U.S. Pat. No. 5,240,707 discloses alpha-mannosidase and fucosidase inhibitors which are speculated to be useful as immunomodulators and as antimetastatic agents. Other known fucosidase inhibitors include L-deoxyfuconojirimycin (DFJ) (Winchester, B. et al., Biochem. J. 265:277-82, 1990), based on the classical nojirimycin imino sugar structure and having an inhibition constant against lysosomal fucosidase of 10 nM. See also U.S. Pat. No. 5,100,797 which discloses additional inhibitors based on deoxyfuconojirimycin (DFJ or DNJ), e.g., beta-L-homofucononojirimycin and 1-beta-C-substituted deoxymannojirimycins. Another potent fucosidase inhibitor is a member of the seven-membered azepane class ((3R,4R,5S,6S)-1-butyl-4,5,6-trihydroxyazepane-3-carboxylic acid, aka "Faz"). Despite having the hydroxyl configuration and carboxyl functionality of an iduronate sugar, this novel molecule also inhibits fucosidase with a potency in the low nanomolar range (Li, H. et al., Chembiochem 9:253-60, 2008). Imino sugar inhibitors having alkyl modification of the amine also have been investigated (McCormack, P. L. et al., Drugs 63:2427-34; discussion 2435-6, 2003; Bause, E. et al., FEBS Lett. 278:167-70, 1991). Fucosidase inhibitors are further described in U.S. Pat. Nos. 5,382,709, 5,240,707, 5,153,325, 5,100,797, 5,096,909 and 5,017,704, U.S. Patent Publication No. 2011/0189084, and Wu et al., Angew. Chem. Int. Ed. 49:337-40 (2010).

SUMMARY

The present disclosure is directed, in general, to compounds, compositions, and methods for treating tumors or cancers, including liver disorders, such as hepatocellular carcinoma. The compositions contemplated comprise a compound as disclosed herein.

In one aspect, the disclosure provides a compound of formula I:

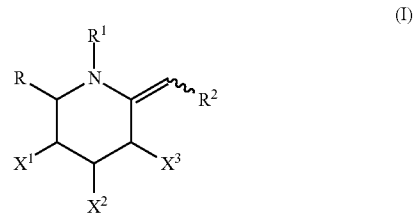

(I)

wherein:
X¹, X², and X³ are independently selected from the group consisting of OH, halo, and O(C)OCH₃;
R is selected from the group consisting of $C_{1-3}$alkyl and $C_{1-3}$haloalkyl;
R¹ is selected from the group consisting of H, $C_{1-3}$alkyl, OH, —CO₂$C_{1-3}$alkyl;
R² is selected from the group consisting of —NR$^b$C(O)R$^a$, —NR$^b$C(O)OR$^a$, —NR$^b$C(O)NR$^c$R$^a$, —NR$^b$C(O)SR$^a$, —C(O)R$^a$, and —C(O)NR$^b$R$^a$;
R$^a$ is —$C_{0-3}$alkylene-G;
G is selected from the group consisting of aryl, heteroaryl, cycloalkyl, and heterocycloalkyl; and
R$^b$ and R$^c$ are independently selected from the group consisting of H and $C_{1-3}$alkyl.

In some embodiments, X¹, X², and X³ are OH.
In some embodiments, R is methyl.
In some embodiments, R¹ is H.
In some embodiments, R² is —NR$^b$C(O)R$^a$.
In some embodiments, R² is —C(O)NR$^b$R$^a$.
In some embodiments, R$^b$ is H.
In some embodiments, G is selected from the group consisting of optionally substituted indolyl, benzothiophenyl, fluorenyl, indenyl, dihydro indenyl, and phenyl.
In some embodiments, G is selected from the group consisting of optionally substituted phenyl and

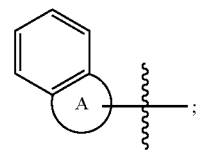

wherein A is a 5-, 6-, 7-, 8-, 9-, or 10-membered carbocyclic or heterocyclic ring system.

In some embodiments, G is selected from the group consisting of

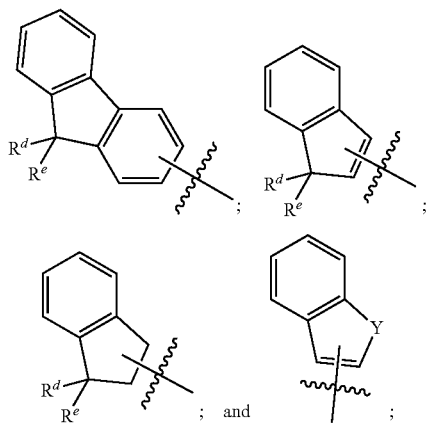

$R^d$ and $R^e$ are independently selected from the group consisting of H, $OR^f$, $NR^fR^g$, $C_{1-3}$alkyl, and $C_{1-5}$cycloalkyl; or $R^d$ and $R^e$ taken together with the carbon atom to which they are attached form C=O;

$R^f$ and $R^g$ are independently selected from the group consisting of H and $C_{1-3}$alkyl; and Y is selected from the group consisting of NH, N—$C_{1-3}$alkyl, S, SO, $SO_2$, and O.

In some embodiments, G is selected from the group consisting of

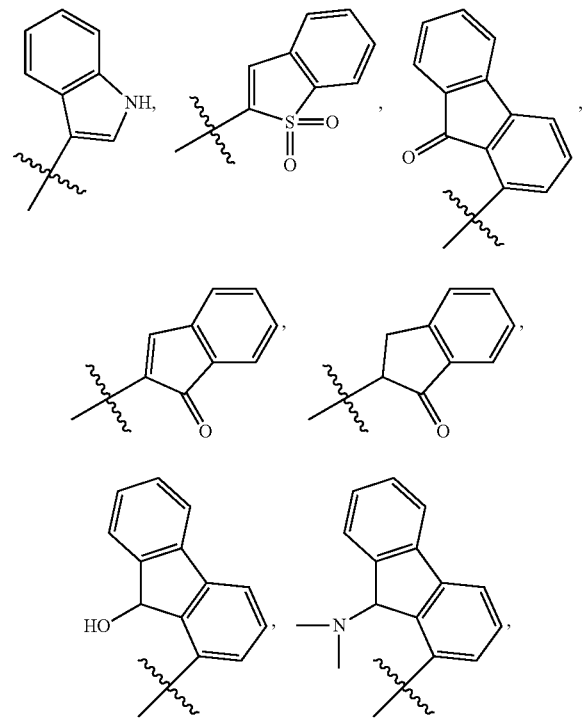

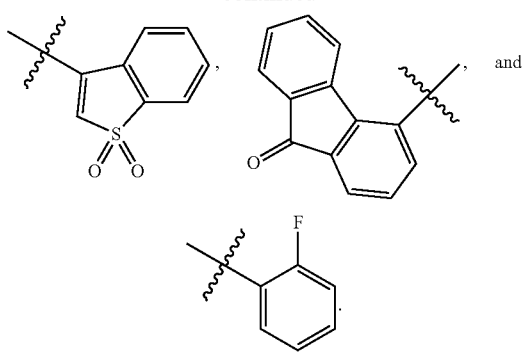

In some embodiments, $R^a$ is selected from the group consisting of

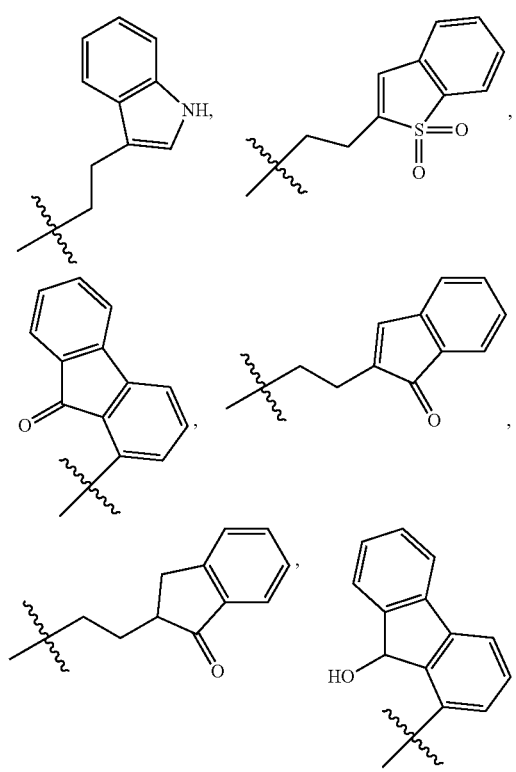

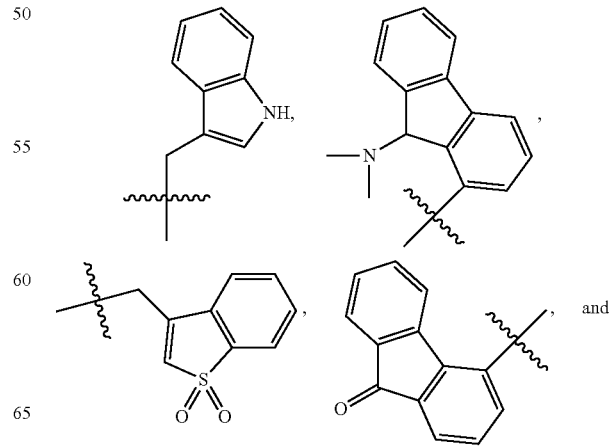

-continued

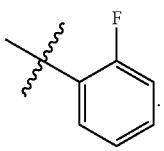

In some embodiments, $R^a$ is

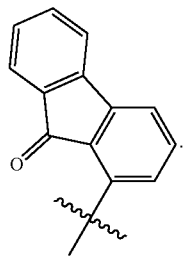 [SMILES: *c1cccc2c1C(=O)c1ccccc1-2]

In some embodiments, the compound of formula I has the following structure:

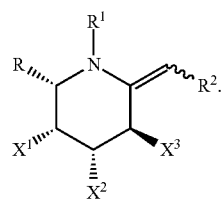

In some embodiments, the compound of formula I has the following structure:

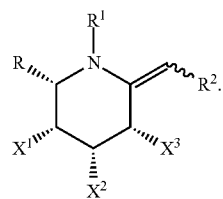

In some embodiments, the compound is selected from the group consisting of:

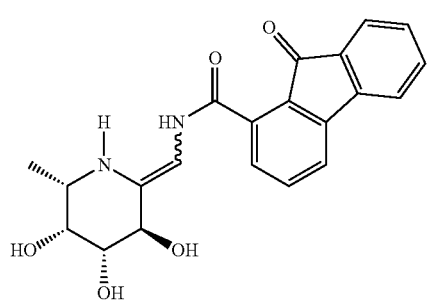

and

-continued

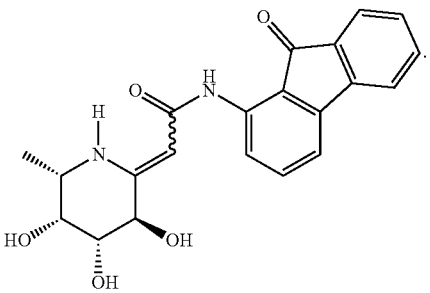

In some embodiments, the compound is selected from the group consisting of:

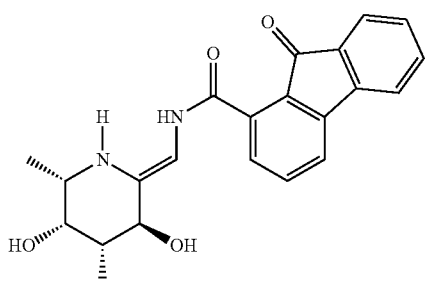

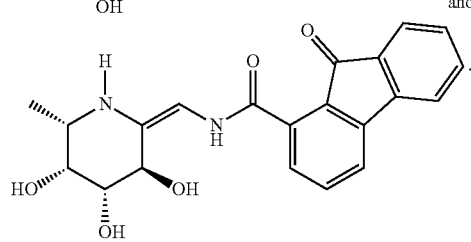

In some embodiments, the compound is selected from the group consisting of:

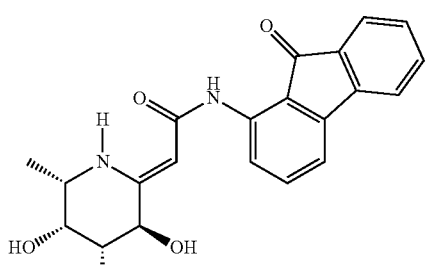

and

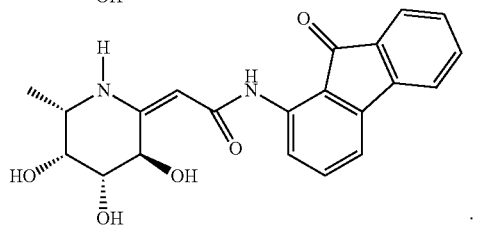

In another aspect, the disclosure provides a method for treating a tumor or cancer in a subject in need thereof comprising administering a compound as described herein in a therapeutically effective amount. In various embodiments, the compound is compound II or compound III:

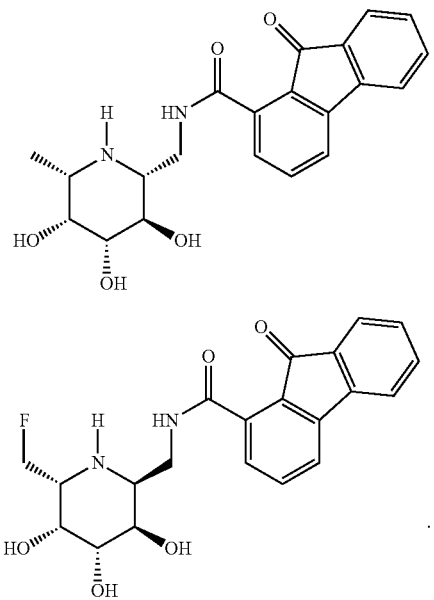

In various embodiments, the tumor or cancer is liver cancer, breast cancer, melanoma, lung cancer, leukemia, pancreatic cancer, gastric cancer, colorectal cancer, and head and neck cancer.

In various embodiments, the compound reduces tumor metastasis in a subject. In a further embodiment, the treatment results in a decrease in tumor size in the subject.

In some embodiments, the tumor is a liver tumor and is a result of hepatocellular carcinoma, hepatitis virus infection, cirrhosis, toxic liver damage, and hereditary hemochromatosis.

In a related embodiment, the liver tumor is a result of hepatocellular carcinoma.

In another embodiment, the treatment results in a reduction of alpha-fetoprotein levels in blood of the subject compared to levels before treatment.

In some embodiments, the compound is administered intravenously. In a related embodiment, the compound is administered via the hepatic artery. In some embodiments, the compound is administered in doses in the range of 0.02 to 2000 mg/kg or 0.1 to 100 mg/kg, for example, 1 to 1500 mg/kg, 10 to 1000 mg/kg, 25 to 500 mg/kg, 50 to 250 mg/kg, 75 to 200 mg/kg, 50 to 150 mg/kg, 60 to 130 mg/kg, 70 to 110 mg/kg, 75 to 100 mg/kg, 80 to 95 mg/kg, 85 to 90 mg/kg, 100 to 250 mg/kg, 120 to 230 mg/kg, 130 to 220 mg/kg, 140 to 210 mg/kg, 150 to 200 mg/kg, 160 to 190 mg/kg, 170 to 180 mg/kg, about 87.5 mg/kg, or about 175 mg/kg.

In some embodiments, the compound is administered in combination with a second agent. In certain embodiments, the second agent is selected from the group consisting of a chemotherapeutic agent, a cytotoxic agent, a radioisotope, an anti-viral agent, an anti-fungal agent, an anti-inflammatory agent and an antibody. In a related embodiment, the chemotherapeutic agent is selected from the group consisting of doxorubicin and 5-fluorouracil.

In a further embodiment, the second agent is a cytotoxic agent. In some embodiments, the cytotoxic agent is selected from the group consisting of mechlorethamine hydrochloride, cyclophosphamide, ifosfamide, chlorambucil, melphalan, busulfan, thiotepa, carmustine, lomustine, dacarbazine and streptozocin.

In another embodiment, the second agent is a radioisotope. In some embodiments, the radioisotope is selected from the group consisting of $^{131}$I, $^{125}$I, $^{111}$In, $^{90}$Y, $^{67}$Cu, $^{127}$Lu, $^{212}$Bi, $^{213}$Bi, $^{255}$Fm, $^{149}$Tb, $^{223}$Rd, $^{213}$Pb, $^{212}$Pb, $^{211}$At, $^{89}$Sr, $^{153}$Sm, $^{166}$Ho, $^{225}$Ac, $^{186}$Re, $^{67}$Ga, $^{68}$Ga and $^{99m}$Tc.

In one embodiment, the tumor is associated with hepatitis virus infection, and the second agent is an antiviral agent.

Use of any of the foregoing compounds disclosed herein in preparation of a medicament for treatment of any of the tumors or cancers described herein is also contemplated. Also contemplated is a composition comprising a compound as described herein for use in treating a tumor or cancer. Syringes, e.g., single use or pre-filled syringes, sterile sealed containers, e.g. vials, bottle, vessel, and/or kits or packages comprising any of the foregoing compounds, optionally with suitable instructions for use, are also contemplated.

Any of the foregoing compounds described herein may be concurrently administered with any agents useful to treat a tumor or cancer known in the art or described herein, as adjunct therapy. Compositions comprising any of the foregoing compounds together with other therapeutic agents (e.g., liver therapy agents) are also contemplated.

It is understood that each feature or embodiment, or combination, described herein is a non-limiting, illustrative example of any of the aspects of the invention and, as such, is meant to be combinable with any other feature or embodiment, or combination, described herein. For example, where features are described with language such as "one embodiment," "some embodiments," "further embodiment," "specific exemplary embodiments," and/or "another embodiment," each of these types of embodiments is a non-limiting example of a feature that is intended to be combined with any other feature, or combination of features, described herein without having to list every possible combination. Such features or combinations of features apply to any of the aspects of the invention. Where examples of values falling within ranges are disclosed, any of these examples are contemplated as possible endpoints of a range, any and all numeric values between such endpoints are contemplated, and any and all combinations of upper and lower endpoints are envisioned.

DETAILED DESCRIPTION

Figure 1:
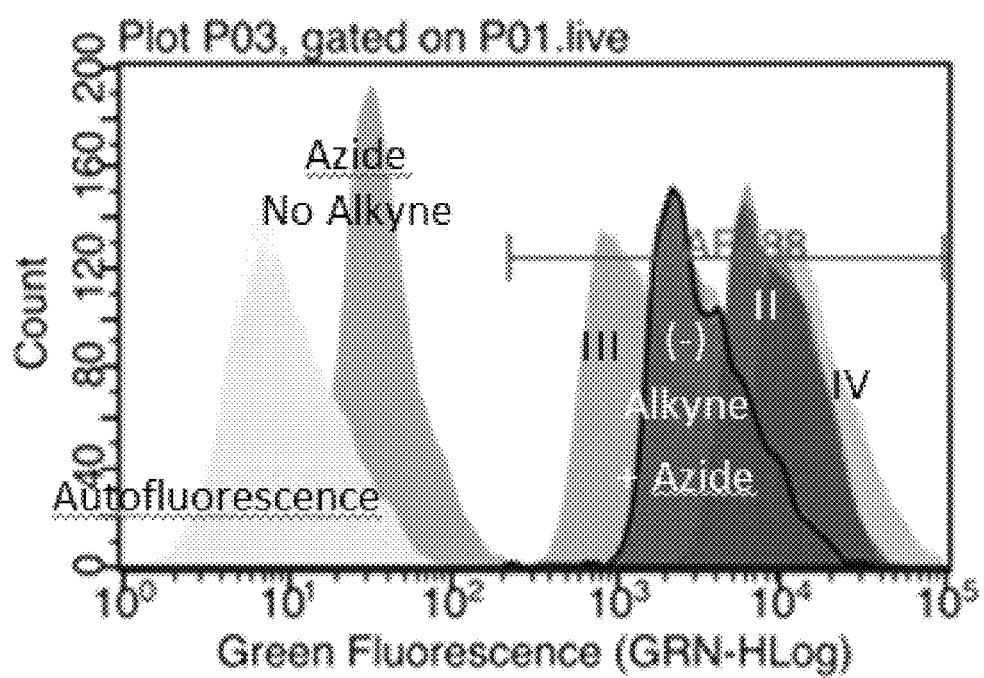
FIG. 1 is a graph showing perturbations in glycoprotein metabolism in HepG2 cells incubated with compounds II, III, and IV.

The present invention relates to compounds and uses of such compounds as fucosidase inhibitors (e.g., as compounds that inhibit the activity of alpha-L-fucosidase to cleave fucose residues from glycoproteins). The present invention also relates to uses of such compounds to treat tumors or cancers, such as liver tumors, particularly hepatocellular carcinoma. Without being bound by a theory of the invention, the fucosidase inhibitors induce glycoprotein-derived oligosaccharide build-up in the lysosome, similar to the effects of a lysosomal storage disease in the liver cell, thereby inducing a cytotoxic event in the cells.

Definitions

As used herein and in the appended claims, the singular forms "a," "an," and "the" include plural referents unless the context clearly dictates otherwise. Thus, for example, reference to "a derivative" includes a plurality of such derivatives and reference to "a patient" includes reference to one or more patients and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and products, the exemplary methods, devices and materials are described herein.

The documents discussed above and throughout the text are provided solely for their disclosure prior to the filing date of the present application. Nothing herein is to be construed as an admission that the inventors are not entitled to antedate such disclosure by virtue of prior disclosure. Each document is incorporated by reference in its entirety with particular attention to the disclosure for which it is cited.

The following references provide one of skill with a general definition of many of the terms used in this disclosure: Singleton, et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger, et al. (eds.), Springer Verlag (1991); and Hale and Marham, THE HARPER COLLINS DICTIONARY OF BIOLOGY (1991).

As used herein, a "therapeutically effective amount" or "effective amount" refers to that amount of the compound sufficient to result in amelioration of symptoms, for example, treatment, healing, prevention or amelioration of the relevant medical condition, or an increase in rate of treatment, healing, prevention or amelioration of such conditions, typically providing a statistically significant improvement in the treated patient population. When referencing an individual active ingredient, administered alone, a therapeutically effective dose refers to that ingredient alone. When referring to a combination, a therapeutically effective dose refers to combined amounts of the active ingredients that result in the therapeutic effect, whether administered in combination, including serially or simultaneously. In some embodiments, such as for fatty liver disease, a therapeutically effective amount of the compound ameliorates one or more symptoms, including but not limited to, liver fibrosis, fat content of liver, incidence of or progression of cirrhosis, incidence of hepatocellular carcinoma, increased hepatic aminotransferase levels, such as ALT and AST, increased serum ferritin, elevated levels of gamma-glutamyltransferase (gamma-GT), and elevated levels of plasma insulin, cholesterol and triglyceride.

"Liver tumors" as used herein includes both primary tumors and/or neoplasia and/or metastases that develop in or on or are physically associated with liver. It also includes metastases of liver tumors that migrate elsewhere in the body, but remain responsive to the compounds disclosed herein. Many types of such tumors and neoplasia are known. Primary liver tumors include hepatocellular carcinoma and others known in the art. Such tumors are generally solid tumors, or they are diffuse tumors with accumulations localized to the liver. Tumors or neoplasia for treatment according to the invention may be malignant or benign, and may have been treated previously with chemotherapy, radiation and/or other treatments.

"Tumors" or "neoplasia" or "cancer" as used herein includes both primary tumors and/or metastases. Tumors include, for example, ovarian, cervical, prostate, breast, lung, colon or gastric carcinomas and metastases thereof to the liver.

"Treatment" refers to prophylactic treatment or therapeutic treatment. In certain embodiments, "treatment" refers to administration of a compound or composition to a subject for therapeutic or prophylactic purposes.

A "therapeutic" treatment is a treatment administered to a subject who exhibits signs or symptoms of pathology for the purpose of diminishing or eliminating those signs or symptoms. The signs or symptoms may be biochemical, cellular, histological, functional or physical, subjective or objective.

A "prophylactic" treatment is a treatment administered to a subject who does not exhibit signs of a disease or exhibits only early signs of the disease, for the purpose of decreasing the risk of developing pathology. The compounds or compositions of the disclosure may be given as a prophylactic treatment to reduce the likelihood of developing a pathology or to minimize the severity of the pathology, if developed.

"Diagnostic" means identifying the presence, extent and/or nature of a pathologic condition. Diagnostic methods differ in their specificity and selectivity. While a particular diagnostic method may not provide a definitive diagnosis of a condition, it suffices if the method provides a positive indication that aids in diagnosis.

"Pharmaceutical composition" refers to a composition suitable for pharmaceutical use in subject animal, including humans and mammals. A pharmaceutical composition comprises a therapeutically effective amount of a compound of the disclosure, optionally another biologically active agent, and optionally a pharmaceutically acceptable excipient, carrier or diluent. In an embodiment, a pharmaceutical composition encompasses a composition comprising the active ingredient(s), and the inert ingredient(s) that make up the carrier, as well as any product that results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the disclosure and a pharmaceutically acceptable excipient, carrier or diluent.

"Pharmaceutically acceptable carrier" refers to any of the standard pharmaceutical carriers, buffers, and the like, such as a phosphate buffered saline solution, 5% aqueous solution of dextrose, and emulsions (e.g., an oil/water or water/oil emulsion). Non-limiting examples of excipients include adjuvants, binders, fillers, diluents, disintegrants, emulsifying agents, wetting agents, lubricants, glidants, sweetening agents, flavoring agents, and coloring agents. Suitable pharmaceutical carriers, excipients and diluents are described in Remington's Pharmaceutical Sciences, 19th Ed. (Mack Publishing Co., Easton, 1995). Preferred pharmaceutical carriers depend upon the intended mode of administration of the active agent. Typical modes of administration include enteral (e.g., oral) or parenteral (e.g., subcutaneous, intramuscular, intravenous or intraperitoneal injection; or topical, transdermal, or transmucosal administration).

A "pharmaceutically acceptable salt" is a salt that can be formulated into a compound for pharmaceutical use, including but not limited to metal salts (e.g., sodium, potassium, magnesium, calcium, etc.) and salts of ammonia or organic amines.

As used herein "pharmaceutically acceptable" or "pharmacologically acceptable" is meant a material that is not biologically or otherwise undesirable, i.e., the material may be administered to an individual without causing any undesirable biological effects or without interacting in a deleterious manner with any of the components of the composition in which it is contained or with any components present on or in the body of the individual.

As used herein, the term "unit dosage form" refers to physically discrete units suitable as unitary dosages for human and animal subjects, each unit containing a predetermined quantity of a compound of the disclosure calculated in an amount sufficient to produce the desired effect, optionally in association with a pharmaceutically acceptable excipient, diluent, carrier or vehicle. The specifications for the novel unit dosage forms of the present disclosure depend on the particular compound employed and the effect to be achieved, and the pharmacodynamics associated with each compound in the host.

As used herein, the term "subject" encompasses mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. The term does not denote a particular age or gender. In various embodiments the subject is human. In various embodiments, the subject is a child or adolescent.

Alpha-L-Fucosidase

The alpha-L-fucosidase enzyme (Genbank Accession No. NP_000138) (herein incorporated by reference) normally participates in the cleavage of long sugar chains (oligosaccharides) in the lysosome. When the enzyme is absent, sugar chains accumulate and eventually lead to the clinical features of fucosidosis. Fucosidosis is an autosomal recessive lysosomal storage disease caused by defective alpha-L-fucosidase with accumulation of the sugar fucose in tissues. See, e.g., Johnson et al., Biochem. Biophys. Res. Commun. 133:90-7, 1986. Different phenotypes include clinical features such as neurologic deterioration, growth retardation, visceromegaly, and seizures in a severe early form; coarse facial features, angiokeratoma corporis diffusum, spasticity and delayed psychomotor development in a longer surviving form.

Fucosidosis can be detected using genetic tests to identify a mutation in the fucosidase gene. Fucosidase is also diagnosed by the presence of increased levels of fucosylated proteins in the urine of fucosidosis patients (Michalski et al., Eur J Biochem. 201: 439-58, 1991).

Alpha-L-fucosidase has been detected at increased levels in hepatocellular carcinoma and has been suggested to be a marker for HCC (Giardina et al., Cancer 70:1044-48, 1992).

Fucosidase Inhibitors

The disclosure provides compounds that interfere with the enzymatic activity of the fucosidase hydrolysis of carbohydrate bonds. The compounds have a structure as provided in formula I:

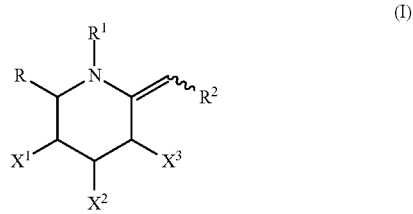

wherein:

$X^1$, $X^2$, and $X^3$ are independently selected from the group consisting of OH, halo, and $O(C)OCH_3$;

R is selected from the group consisting of $C_{1-3}$alkyl and $C_{1-3}$haloalkyl;

$R^1$ is selected from the group consisting of H, $C_{1-3}$alkyl, OH, $-CO_2C_{1-3}$alkyl;

$R^2$ is selected from the group consisting of $-NR^bC(O)R^a$, $-NR^bC(O)OR^a$, $-NR^bC(O)NR^cR^a$, $-NR^bC(O)SR^a$, $-C(O)R^a$, and $-C(O)NR^bR^a$;

$R^a$ is $-C_{0-3}$alkylene-G;

G is selected from the group consisting of aryl, heteroaryl, cycloalkyl, and heterocycloalkyl; and $R^b$ and $R^c$ are independently selected from the group consisting of H and $C_{1-3}$alkyl.

In some cases, $X^1$, $X^2$, and $X^3$ are OH, R is methyl, and/or $R^1$ is H. In some cases, $R^2$ is $-NR^bC(O)R^a$ or $-C(O)NR^bR^a$. In some cases, $R^b$ is H.

Suitable G groups include, but are not limited to, optionally substituted indolyl, benzothiophenyl, fluorenyl, indenyl, dihydro indenyl, and phenyl. For example, G groups include optionally substituted phenyl and

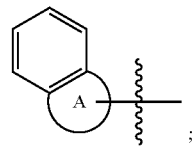

wherein A is a 5-, 6-, 7-, 8-, 9-, or 10-membered carbocyclic or heterocyclic ring system.

G groups also include, but are not limited to,

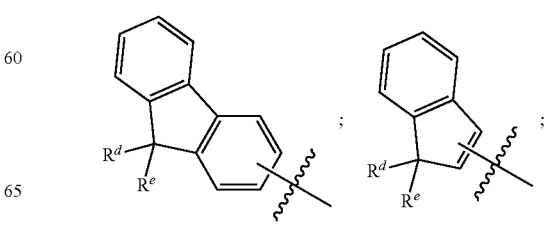

-continued

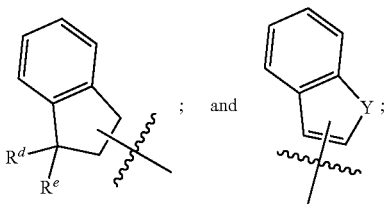

wherein $R^d$ and $R^e$ are independently selected from the group consisting of H, $OR^f$, $NR^fR^g$, $C_{1-3}$alkyl, and $C_{1-5}$cycloalkyl; or $R^d$ and $R^e$ taken together with the carbon atom to which they are attached form C=O;

$R^f$ and $R^g$ are independently selected from the group consisting of H and $C_{1-3}$alkyl; and Y is selected from the group consisting of NH, N—$C_{1-3}$alkyl, S, SO, $SO_2$, and O.

Examples of G groups include, but are not limited to, the following:

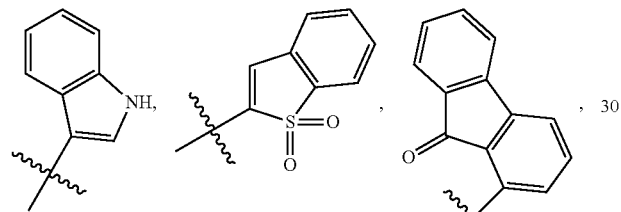

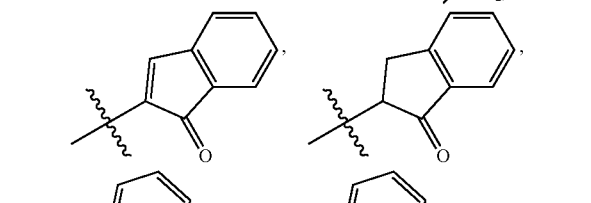

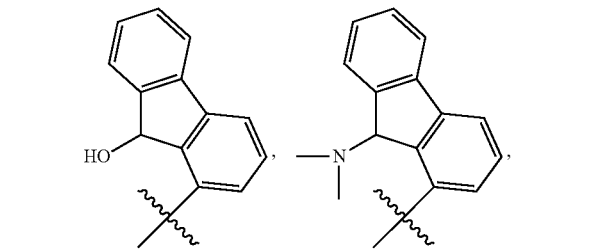

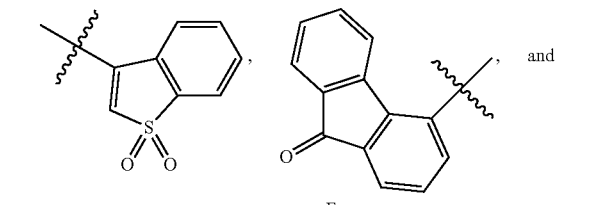

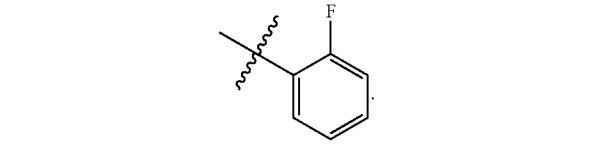

Examples of $R^a$ groups include, but are not limited to, the following:

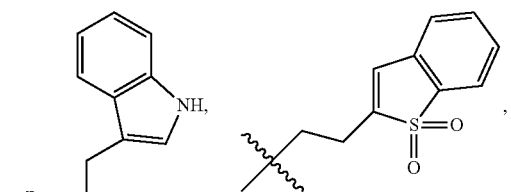

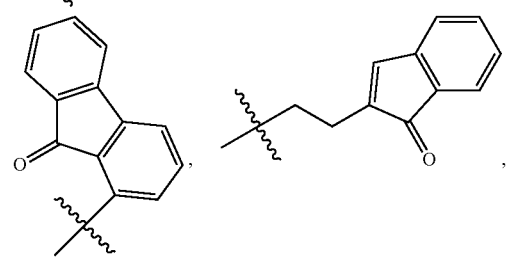

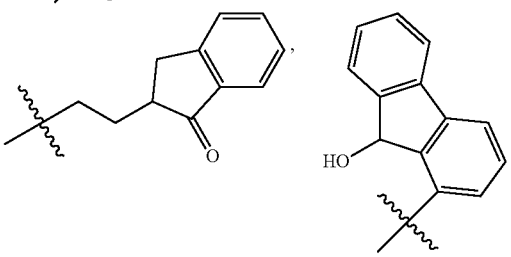

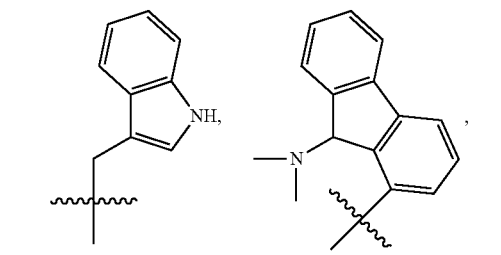

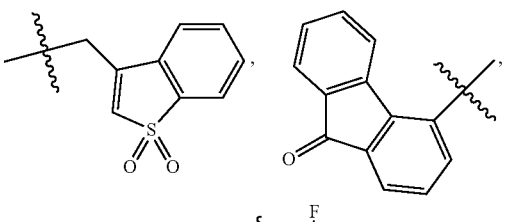

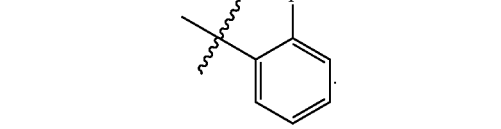

In some cases, the compound of formula I has the following structure:

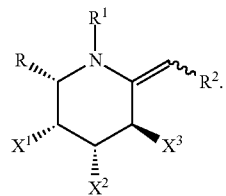

In some cases, the compound of formula I has the following structure:

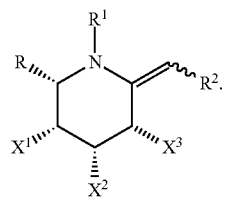

Suitable compounds include, but are not limited to:

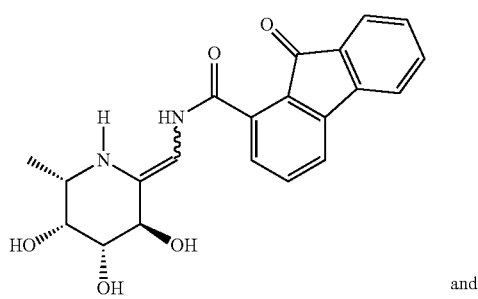

and

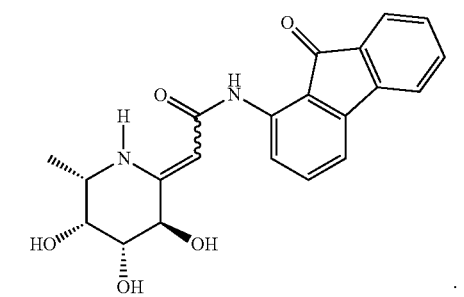

Examples of compounds also include, but are not limited to:

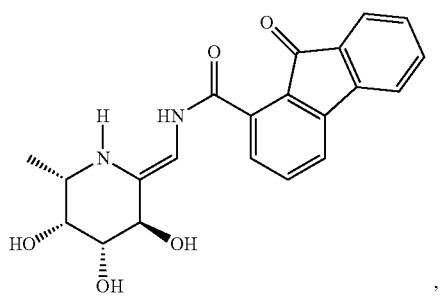

,

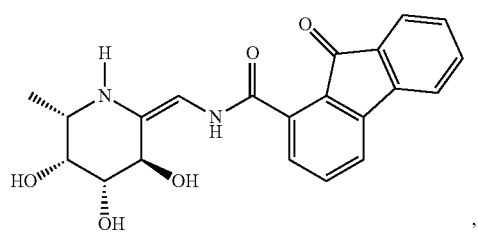

,

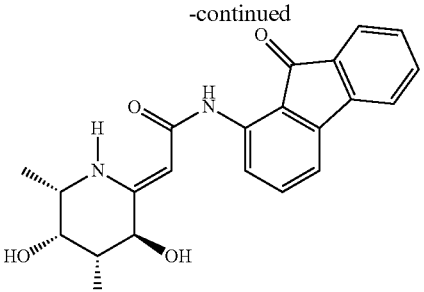

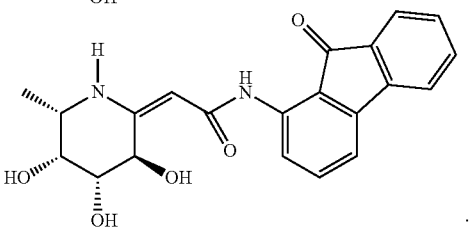

and

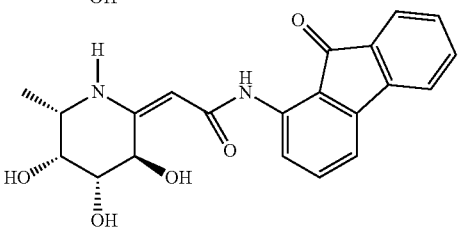

.

Methods of Using, Pharmaceutical Compositions, and Administration

The compounds can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Unit dosage forms for injection or intravenous administration may comprise the compound in a composition as a solution in sterile water, sterile normal saline or another sterile pharmaceutically acceptable carrier.

In practical use, the compounds described herein can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous).

With respect to transdermal routes of administration, methods for transdermal administration of drugs are disclosed in Remington's Pharmaceutical Sciences, 17th Edition, (Gennaro et al. Eds. Mack Publishing Co., 1985). Dermal or skin patches are one means for transdermal delivery of the compounds useful in the methods of the invention. Patches preferably provide an absorption enhancer such as DMSO to increase the absorption of the compounds. Other methods for transdermal drug delivery are disclosed in U.S. Pat. Nos. 5,962,012, 6,261,595, and 6,261,595. Each of which is incorporated by reference in its entirety.

Pharmaceutically acceptable excipients, such as vehicles, adjuvants, carriers or diluents, are commercially available. Moreover, pharmaceutically acceptable auxiliary substances, such as pH adjusting and buffering agents, tonicity adjusting agents, stabilizers, wetting agents and the like, are commercially available.

Those of skill will readily appreciate that dose levels can vary as a function of the specific compound, the severity of the symptoms and the susceptibility of the subject to side effects. Preferred dosages for a given compound are readily determinable by those of skill in the art by a variety of means, including, but not limited to dose response and pharmacokinetic assessments conducted in patients, test animals, and in vitro.

In each of these aspects, the compositions include, but are not limited to, compositions suitable for oral, rectal, topical, parenteral (including subcutaneous, intramuscular, and intravenous), pulmonary (nasal or buccal inhalation), or nasal administration, although the most suitable route in any given case will depend in part on the nature and severity of the conditions being treated and on the nature of the active ingredient. Exemplary routes of administration are the oral and intravenous routes. The compositions may be conveniently presented in unit dosage form and prepared by any of the methods well-known in the art of pharmacy.

Compositions of the present invention may be administered encapsulated in or attached to viral envelopes or vesicles, or incorporated into cells. Vesicles are micellular particles which are usually spherical and which are frequently lipidic. Liposomes are vesicles formed from a bilayer membrane. Suitable vesicles include, but are not limited to, unilamellar vesicles and multilamellar lipid vesicles or liposomes. Such vesicles and liposomes may be made from a wide range of lipid or phospholipid compounds, such as phosphatidylcholine, phosphatidic acid, phosphatidylserine, phosphatidylethanolamine, sphingomyelin, glycolipids, gangliosides, etc. using standard techniques, such as those described in, e.g., U.S. Pat. No. 4,394,448. Such vesicles or liposomes may be used to administer compounds intracellularly and to deliver compounds to the target organs. Controlled release of a composition of interest may also be achieved using encapsulation (see, e.g., U.S. Pat. No. 5,186,941).

Any route of administration that delivers the compound into the blood stream may be used. Preferably, the composition is administered parenterally, most preferably intravenously. In some embodiments, the composition is administered via portal vein. Intrajugular and intracarotid injections are also useful. Compositions may be administered locally or regionally, such as intraperitoneally or subcutaneously on intramuscularly. In one aspect, compositions are administered with a suitable pharmaceutical diluent or carrier.

Dosages to be administered will depend on individual needs, on the desired effect, the active agent used, and on the chosen route of administration. Preferred dosages of a compound range from about 0.2 pmol/kg to about 25 nmol/kg, and particularly preferred dosages range from 2-250 pmol/kg; alternatively, preferred doses of the compound may be in the range of 0.02 to 2000 mg/kg or 0.1 to 100 mg/kg, for example, 1 to 1500 mg/kg, 10 to 1000 mg/kg, 25 to 500 mg/kg, 50 to 250 mg/kg, 75 to 200 mg/kg, 50 to 150 mg/kg, 60 to 130 mg/kg, 70 to 110 mg/kg, 75 to 100 mg/kg, 80 to 95 mg/kg, 85 to 90 mg/kg, 100 to 250 mg/kg, 120 to 230 mg/kg, 130 to 220 mg/kg, 140 to 210 mg/kg, 150 to 200 mg/kg, 160 to 190 mg/kg, 170 to 180 mg/kg, about 87.5 mg/kg, or about 175 mg/kg.

The compounds of the invention are useful for therapeutic, prophylactic and diagnostic intervention in animals, e.g. mammals, and in particular in humans.

The subject methods find use in the treatment of a variety of different disease conditions. The specific disease conditions treatable with the subject compounds are varied. Thus, disease conditions which affect the liver and treatable by the methods of the invention include cellular proliferative diseases, such as neoplastic diseases, autoimmune diseases, hormonal abnormality diseases, degenerative diseases, diseases of aging, and the like which can result in growth of liver tumors.

Treatment is meant to encompass any beneficial outcome to a subject associated with administration of a compound including a reduced likelihood of acquiring a disease, prevention of a disease, slowing, stopping or reversing, the progression of a disease or an amelioration of the symptoms associated with the disease condition afflicting the host, where amelioration or benefit is used in a broad sense to refer to at least a reduction in the magnitude of a parameter, e.g., symptom, associated with the pathological condition being treated, such as inflammation and pain associated therewith. As such, treatment also includes situations where the pathological condition, or at least symptoms associated therewith, are completely inhibited, e.g., prevented from happening, or stopped, e.g., terminated, such that the host no longer suffers from the pathological condition, or at least the symptoms that characterize the pathological condition.

Cancer

It is contemplated herein that inhibitors of fucosidase are useful to treat cancers determined to be sensitive to treatment with a fucosidase inhibitor. It is contemplated that the methods herein are useful to identify cancers that are resistant to treatment with fucosidase inhibitors. Exemplary cancers include but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, including triple negative breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor. In some embodiments, the cancer is selected from the group consisting of melanoma, colorectal cancer, pancreatic cancer, bladder cancer, breast cancer, triple negative breast cancer, ovarian cancer and lung cancer.

In various embodiments, the tumor or cancer is liver cancer, breast cancer, melanoma, lung cancer, leukemia, pancreatic cancer, gastric cancer, colorectal cancer, or head and neck cancer.

Liver Disorders

Liver diseases or liver disorders contemplated by the invention include, but are not limited to, those disorders discussed below. Hepatocellular carcinoma, or hepatoma, is the fifth most common cancer in the world and incidence rates have been climbing steadily. Tumorigenic hepatocytes retain high levels of LRP1 expression. Hepatocellular carcinoma does not respond well to chemotherapy because the tumor cells show high rates of drug resistance and because the chemotherapies used have serious toxicities, especially in the heart and kidney, due to systemic (intravenous) administration.

Hepatitis is a generic term for inflammation of the liver. Hepatitis can be acute or chronic and includes acute or chronic liver failure, e.g., due to virus (e.g., hepatitis A, B, C, D or E or non-ABCDE, CMV, Epstein-Barr), fungal, rickettsial or parasitic infections, alcohol, chemical toxins, drugs (e.g. acetaminophen, amiodarone, isoniazid, halothane, chlorpromazine, erythromycin), metabolic liver disease (e.g., Wilson's disease, alpha1-antitrypsin deficiency), cancer, idiopathic autoimmune liver disease, cirrhosis (e.g. primary biliary cirrhosis), biliary obstruction. Infection of the liver by Hepatitis A, B and/or C virus can lead to slowly progressing liver disease leading to liver failure. Acute hepatitis infection is most commonly caused by hepatitis A. Both hepatitis B and hepatitis C infection can persist in the body and become longstanding infections (chronic). Hepatitis C can cause critical conditions including cirrhosis and cancer.

Additional liver disorders or conditions contemplated that are treatable using the compounds disclosed herein include tumors associated with or resulting from hepatic steatitis, cholestasis, liver cirrhosis, toxic liver damage (e.g., due to drug toxicity or environmental toxicity, such as Aflatoxin B1 associated cancer) and hereditary hemochromatosis.

It is contemplated that administration of the compounds disclosed herein to subjects having a liver tumor is done in combination with a second agent, including, but not limited to chemotherapeutic agents, cytotoxic agents, radioisotopes, anti-virals, anti-fungals, anti-inflammatories, antibodies and other therapies useful to treat liver tumors or other liver diseases associated with development of liver tumors.

Candidate drugs for administration to HCC patients in combination with the compounds disclosed herein for the treatment of liver carcinoma include, but are not limited to: 5-fluorouracil, doxorubicin (adriamycin), mitomycin C, cisplatin, epirubicin, daunorubicin, etoposide, and other chemotherapeutic agents set out in Table 1, adefovir, lamivudine, entecavir, ribavirin, interferon alpha, pegylated interferon alpha-2a, interferon alpha-2b and other antivirals, Vitamin E, ursodeoxycholic acid, and other agents used to treat liver disorders. Additional agents are shown in Table 1.

TABLE 1

| Alkylating agents | Natural products |
|---|---|
| Nitrogen mustards | Antimitotic drugs |
| mechlorethamine | Taxanes |
| cyclophosphamide | paclitaxel |
| ifosfamide | Vinca alkaloids |
| melphalan | vinblastine (VLB) |
| chlorambucil | vincristine |
| Nitrosoureas | vinorelbine |
| carmustine (BCNU) | Taxotere ® (docetaxel) |
| lomustine (CCNU) | estramustine |
| semustine (methyl-CCNU) | estramustine phosphate |
| Ethylenimine/Methyl-melamine | Epipodophylotoxins |
| thriethylenemelamine (TEM) | etoposide |
| triethylene thiophosphoramide (thiotepa) | teniposide |
|  | Antibiotics |
| hexamethylmelamine (HMM, altretamine) | actimomycin D |
|  | daunomycin (rubido-mycin) |
| Alkyl sulfonates | doxorubicin (adria-mycin) |
| busulfan | mitoxantroneidarubicin |
| Triazines | bleomycin |
| dacarbazine (DTIC) | splicamycin (mithramycin) |
| Antimetabolites | mitomycinC |
| Folic Acid analogs | dactinomycin |
| methotrexate | aphidicolin |
| Trimetrexate | Enzymes |
| Pemetrexed | L-asparaginase |
| (Multi-targeted antifolate) | L-arginase |
| Pyrimidine analogs | Radiosensitizers |
| 5-fluorouracil | metronidazole |
| fluorodeoxyuridine | misonidazole |
| gemcitabine | desmethylmisonidazole |
| cytosine arabinoside | pimonidazole |
| (AraC, cytarabine) | etanidazole |
| 5-azacytidine | nimorazole |
| 2,2'-difluorodeoxy-cytidine | RSU 1069 |
| Purine analogs | EO9 |
| 6-mercaptopurine | RB 6145 |
| 6-thioguanine | SR4233 |
| azathioprine | nicotinamide |

TABLE 1-continued

| | |
|---|---|
| 2'-deoxycoformycin (pentostatin) erythrohydroxynonyl-adenine (EHNA) fludarabine phosphate | 5-bromodeozyuridine 5-iododeoxyuridine bromodeoxycytidine Miscellaneous agents |
| 2-chlorodeoxyadenosine (cladribine, 2-CdA) Type I Topoisomerase Inhibitors | Platinium coordination complexes cisplatin |
| camptothecin topotecan irinotecan Biological response modifiers | Carboplatin oxaliplatin Anthracenedione mitoxantrone |
| G-CSF | Substituted urea |
| GM-CSF Differentiation Agents | hydroxyurea Methylhydrazine derivatives |
| retinoic acid derivatives Hormones and antagonists | N-methylhydrazine (MIH) procarbazine |
| Adrenocorticosteroids/antagonists | Adrenocortical suppressant |
| prednisone and equivalents dexamethasone ainoglutethimide | mitotane (o,p'-DDD) ainoglutethimide Cytokines |
| Progestins | interferon (α, β, γ) |
| hydroxyprogesterone caproate medroxyprogesterone acetate | interleukin-2 Photosensitizers |
| megestrol acetate Estrogens | hematoporphyrin derivatives Photofrin ® |
| diethylstilbestrol ethynyl estradiol/equivalents Antiestrogen | benzoporphyrin derivatives Npe6 tin etioporphyrin (SnET2) |
| tamoxifen Androgens | pheoboride-a bacteriochlorophyll-a |
| testosterone propionate fluoxymesterone/equivalents Antiandrogens | naphthalocyanines phthalocyanines zinc phthalocyanines |
| flutamide | Radiation |
| gonadotropin-releasing hormone analogs leuprolide Nonsteroidal antiandrogens | X-ray ultraviolet light gamma radiation visible light |
| flutamide | infrared radiation microwave radiation |

Cytotoxic agents useful to treat tumors include, but are not limited to, Mechlorethamine hydrochloride, Cyclophosphamide, Ifosfamide, Chlorambucil, Melphalan, Busulfan, Thiotepa, Carmustine, Lomustine, Dacarbazine and Streptozocin.

Radioisoptoes useful to treat tumors include, but are not limited to, $^{131}$I, $^{125}$I, $^{111}$In, $^{90}$Y, $^{67}$Cu, $^{127}$Lu, $^{212}$Bi, $^{213}$Bi, $^{255}$Fm, $^{149}$Tb, $^{223}$Rd, $^{213}$Pb, $^{212}$Pb, $^{211}$At, $^{89}$Sr, $^{153}$Sm, $^{166}$Ho, $^{225}$Ac, $^{186}$Re, $^{67}$Ga, $^{68}$Ga and $^{99m}$Tc.

Antibodies contemplated for use in the methods include those used to treat cancer and other disorders, including but not limited to, anti-epidermal growth factor receptor (EGFR) (cituximab, panitumamab), anti-platelet derived growth factor receptor alpha (PDGFRalpha), anti-glypican 3 (GPC3), and other antibodies useful to treat cancer or cancer that has metastasized to the liver and other areas of the body.

Kits

As an additional aspect, the invention includes kits which comprise one or more compounds or compositions described herein packaged in a manner which facilitates their use to practice methods of the invention. In one embodiment, such a kit includes a compound or composition described herein (e.g., a composition comprising a compound alone or in combination with a second agent), packaged in a container such as a sealed bottle or vessel, with a label affixed to the container or included in the package that describes use of the compound or composition in practicing the method. Preferably, the compound or composition is packaged in a unit dosage form. The kit may further include a device suitable for administering the composition according to a specific route of administration. Preferably, the kit contains a label that describes use of the composition.

While the disclosure has been described in conjunction with specific embodiments thereof, the foregoing description as well as the examples which follow are intended to illustrate and not limit the scope of the disclosure. Other aspects, advantages and modifications within the scope of the disclosure will be apparent to those skilled in the art.

EXAMPLES

Example 1

Synthesis of Compounds

The compounds disclosed herein can be prepared according to the following methods, using suitable modifications to the starting reagents. One of skill in the art, in view of the teachings below and using typical organic chemistry techniques, can synthesize a compound as disclosed herein.

Synthesis of Intermediate A:

Intermediate A was prepared from D-glucose as shown in Scheme 1.

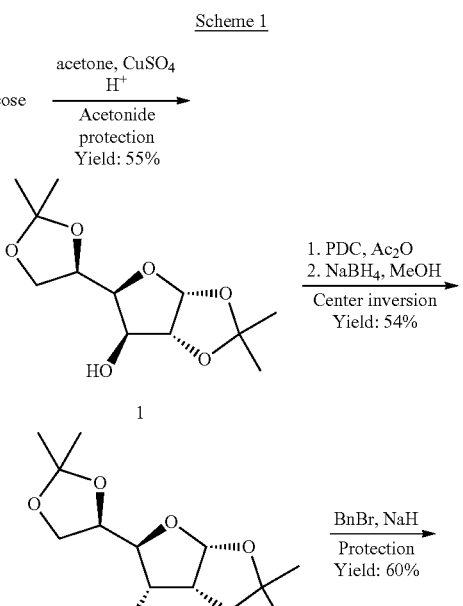

Scheme 1

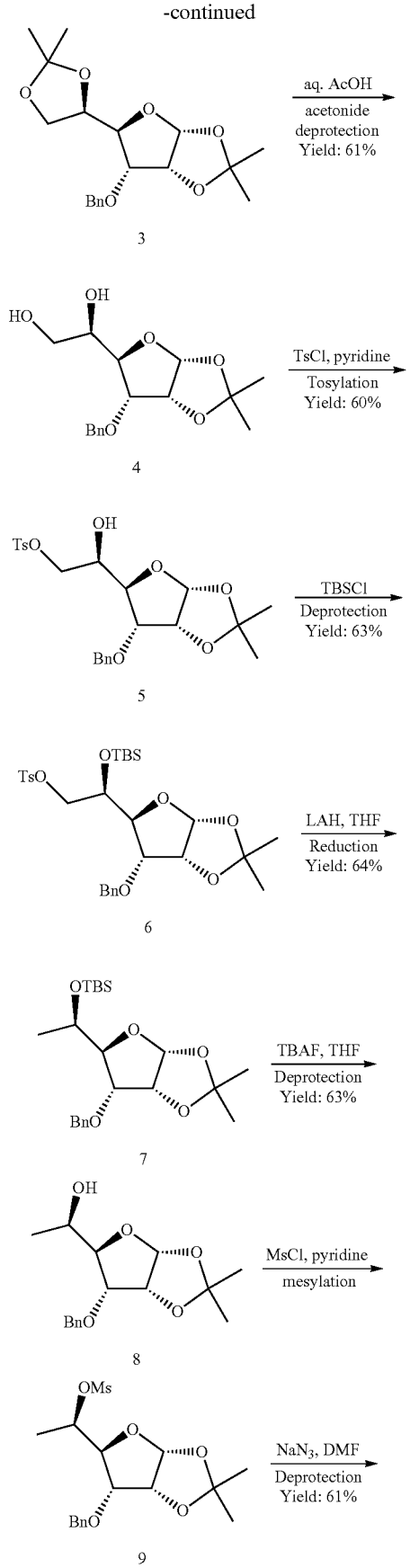
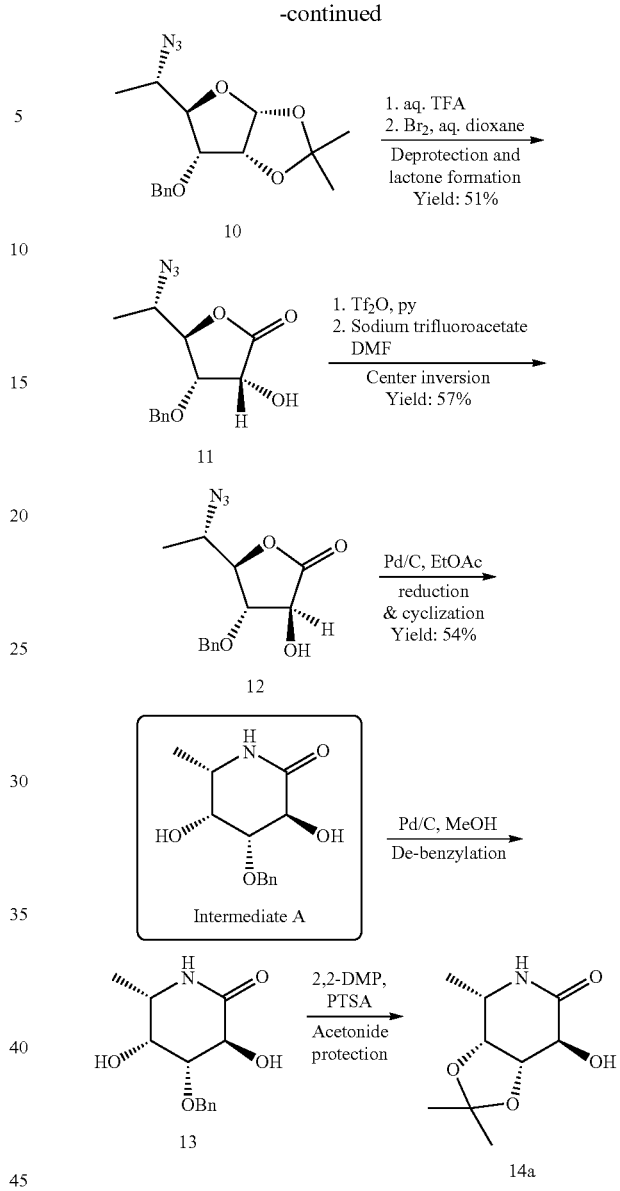
De-benzylation of Intermediate A results in compound 13, which can be converted to protected compound 14a.
Synthesis of Compounds of Formula I:
Compounds of Formula I are prepared from compound 13 by conversion to an enamine (compound 16), followed by coupling with an appropriate activated carboxylic acid as shown in Scheme 2.
Scheme 2
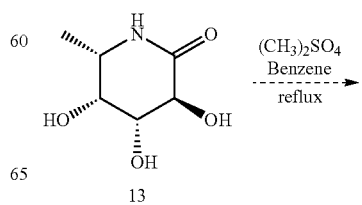

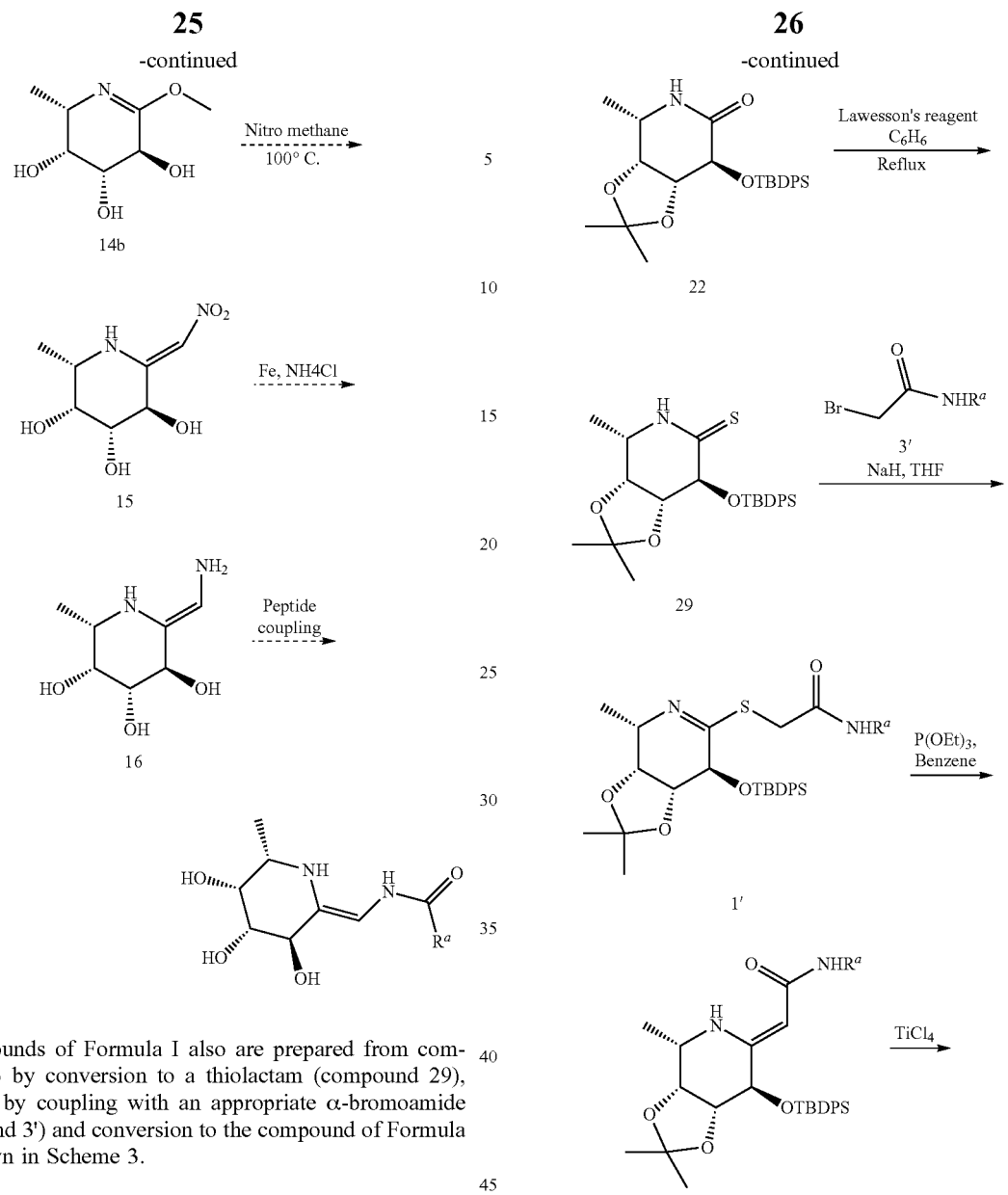
Compounds of Formula I also are prepared from compound 13 by conversion to a thiolactam (compound 29), followed by coupling with an appropriate α-bromoamide (compound 3') and conversion to the compound of Formula I as shown in Scheme 3.
Scheme 3
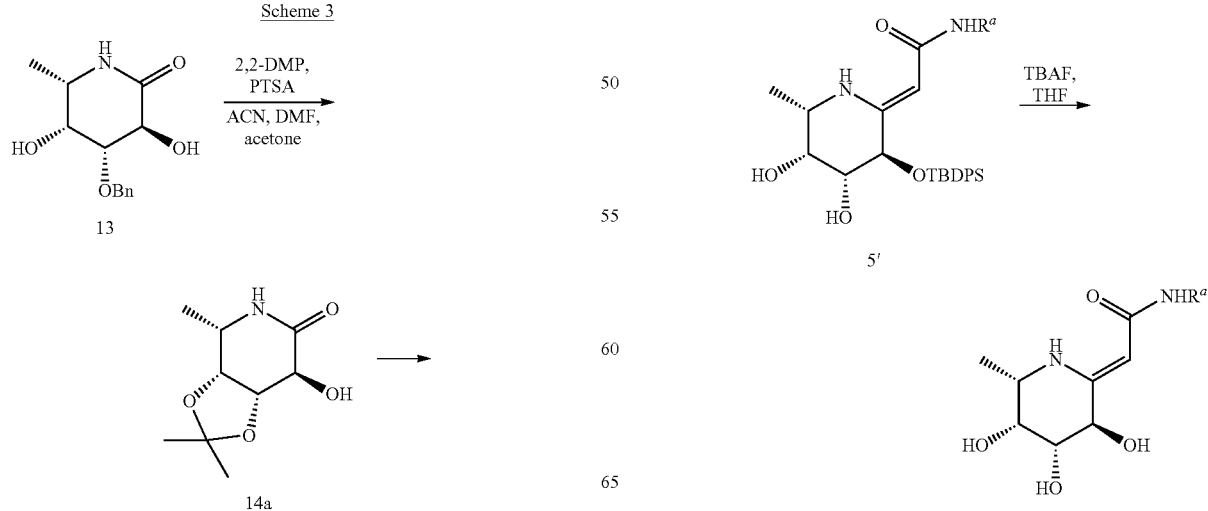

Example 2

In Vitro Fucosidase Inhibition

Fucosidase inhibition was assessed by preparing a reaction mixture of 50 mM phosphate-citrate pH 4.5, 5 mM $MgCl_2$, 640 nM 4-methylumbelliferyl-alpha-L-fucopyranoside (4MU-FUC), 1 ng/mL rhFUCA1 (R&D Systems), and compound II, III, or IV:

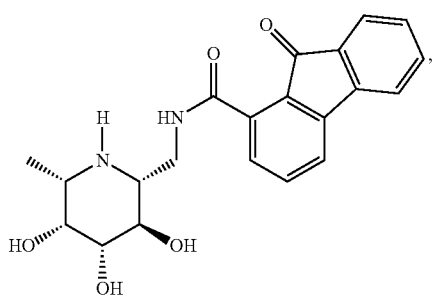

II

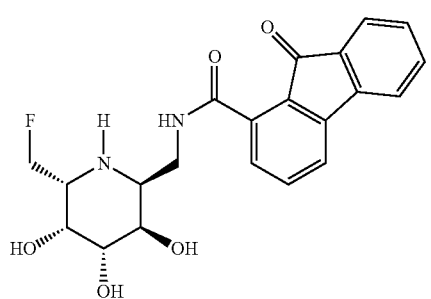

III

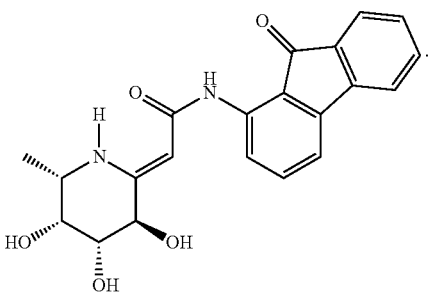

IV

Reactions (100 μL) were incubated at 37° C. for 30 minutes and then quenched with the same volume of 600 mM citrate-carbonate buffer, pH 9. Fluorescence was measured by excitation at 360 nm and emission at 450 nm. The results are provided in Table 2.

TABLE 2

| Compound | In vitro IC50 (μM) |
|---|---|
| II | 0.016 |
| III | 0.059 |
| IV | 1.5 |

The results demonstrate effective inhibition of fucosidase activity by compounds II, III and IV.

Example 3

Metabolic Labeling with Tagged-Fucose

Perturbations in glycoprotein metabolism were assayed by growing HepG2 cells without fucosidase inhibitors, or with compound II, III, or IV (see Example 2) for 24 hours, and then adding (3S,4R,5R,6S)-6-ethynyltetrahydro-2H-pyran-2,3,4,5-tetrayl tetra acetate, a per-acetylated analog of fucose containing an alkyne moiety in place of the 5'-methyl group (Click-iT™ Fucose Alkyne, Molecular Probes, Eugene, Oreg.) for an additional 48 hours. Cells were fixed, permeabilized, washed, and stained with Alexa Fluor 488 Azide to orthogonally label glycoproteins incorporating the fucose analog. Cells were then analyzed for fluorescence using a Guava 6HT-2L flow cytometer (ThermoFisher). The results are provided in FIG. 1 and Table 3, and demonstrate increased levels of fucosylated material in cells upon treatment with compounds II and IV, consistent with fucosidase inhibition. The results also demonstrate decreased levels of fucosylated material in cells treated with compound III, suggesting possible inhibition of fucosylation. Further, in a similar assay using healthy fibroblast cells in place of HepG2 cells, treatment with compound II demonstrated minimal effect on levels of fucosylated material.

TABLE 3

| Sample | Mean Green Fluorescence (GRN-HLog) | Fold over vehicle |
|---|---|---|
| Vehicle ((−) Alkyne + Azide) | 2831 | — |
| Compound II | 8433 | 2.98 |
| Compound IV | 12900 | 4.56 |
| Compound III | 1220 | 0.43 |

Example 4

Cytotoxicity in HepG2 Cells

Figure 2:
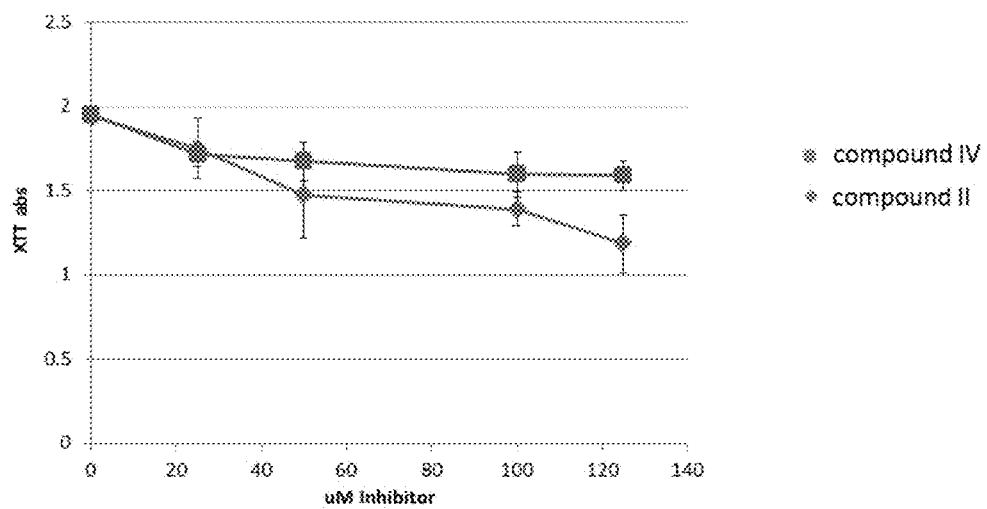
FIG. 2 is a graph showing cytotoxicity of compounds II and IV in HepG2 cells after 24 hours of treatment.
Figure 3:
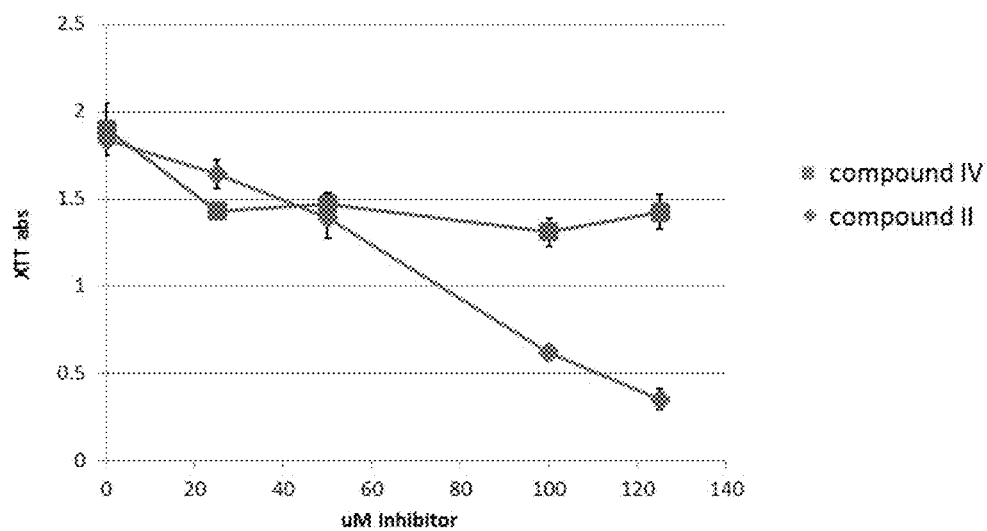
FIG. 3 is a graph showing cytotoxicity of compounds II and IV in HepG2 cells after 48 hours of treatment.

To assess the compounds' cytotoxicity in cells, HepG2 cells were seeded in triplicate in 96-well plates at 1.5e4 cells/well in Minimum Essential Media, 10% FBS and 2 mM L-glutamine. Plated cells were allowed to recover for 48 hours. Medium was then replaced with the same media containing dilutions of compound II or IV (see Example 2), incubated for 24 or 48 hours, and subjected to XTT assay to measure viability (ATCC). The results are provided in FIG. 2 and FIG. 3 and show that compound IV demonstrates reduced cytotoxicity at higher inhibitor concentrations compared to compound II.

Example 5

Cytotoxicity of Compound II

Multiplexed Cytotoxicity Assay:

To assess the cytotoxicity of compound II (see Example 2) in cancer and normal cells, the cells were grown in RPMI1640, 10% FBS, 2 mM L-alanyl-L-Glutamine, 1 mM Na Pyruvate or a special medium in a humidified atmosphere of 5% $CO_2$ at 37° C. Cells were seeded into 384-well plates and incubated in a humidified atmosphere of 5% $CO_2$ at 37° C. Compound II was added 24 hours post cell seeding. At the same time, a time zero untreated cell plate was generated.

After a 72 hour incubation period, cells were fixed and stained with fluorescently labeled antibodies and nuclear dye to allow visualization of nuclei, apoptotic cells and mitotic cells. Apoptotic cells were detected using an anti-active caspase-3 antibody. Mitotic cells were detected using an anti phospho-histone-3 antibody.

Compound II was serially diluted 3.16-fold and assayed over 9 concentrations. Automated fluorescence microscopy was carried out using a GE Healthcare IN Cell Analyzer 1000, and images were collected with a 4× objective.

Data Analysis:

Twelve bit tiff images were acquired using the InCell Analyzer 1000 3.2 and analyzed with Developer Toolbox 1.6 software. $EC_{50}$ and $IC_{50}$ values were calculated using non-linear regression to fit data to a sigmoidal 4 point, 4 parameter One-Site dose response model, where: y (fit)=A+ [(B−A)/(1+((C/x)^D))]. Curve-fitting, $EC_{50}$/$IC_{50}$ calculations and report generation are performed using a custom data reduction engine MathIQ based software (AIM).

The multiplexed cytotoxicity assay uses a cell image based analysis technique where cells are fixed and stained with fluorescently labeled antibodies and nuclear dye to visualize nuclei, and apoptotic and mitotic cells. Apoptotic cells are detected using an anti-active caspase-3 antibody. Mitotic cells are detected using an anti phospho-histone-3 antibody. Cell proliferation is measured by the signal intensity of the incorporated nuclear dye. The cell proliferation assay output is referred to as the relative cell count. To determine the cell proliferation end point, the cell proliferation data output is transformed to percent of control (POC) using the following formula:

POC=relative cell count (compound wells)/relative cell count (vehicle wells)×100.

Relative cell count $IC_{50}$ is the test compound concentration at 50% of maximal possible response. A relative cell count $EC_{50}$ is the test compound concentration at the curve inflection point or half the effective response (parameter C of the fitted curve solution). $GI_{50}$ is the concentration needed to reduce the observed growth by half. This is the concentration that inhibits the growth midway between untreated cells and the number of cells seeded in the well (Time zero value).

Time zero non-treated plate is used to determine number of doublings in 72 hour assay period: Number of doublings in 72 hours=LN[Cell number (72 hrs end point)*Cell number (time zero)]/LN(2)

The output of each biomarker is fold increase over vehicle background normalized to the relative cell count in each well.

The activated caspase-3 marker labels cells from early to late stage apoptosis. The output is shown as a fold increase of apoptotic cells over vehicle background normalized to the relative cell count in each well. Concentrations of test compound that cause a 5-fold induction in the caspase-3 signal indicates significant apoptosis induction. Wells with concentrations higher than the relative cell count $IC_{95}$ are eliminated from the caspase 3 induction analysis.

The phospho-histone-3 marker labels mitotic cells. The output is shown as a fold induction of mitotic cells over vehicle background normalized to the relative cell count in each well. When the fold induction of mitotic cell signal over background is ~1, there is "no effect" on the cell cycle. Two or more fold increase in phospho-histone-3 signal over vehicle background indicates significant test compound induction of mitotic block.

Two or more fold decrease in the phospho-histone-3 signal may indicate G1/S block only when cytotoxicity levels are below the measured relative cell count $IC_{95}$. When two or more fold decrease in the phospho-histone-3 signal are observed at concentrations higher than the relative cell count $IC_{95}$, the decrease in mitotic cell counts are most likely due to a more general cytotoxicity effect rather than a true G1/S phase block. Wells with concentrations higher than the relative cell count $IC_{95}$ are eliminated from the phospho-histone-3 analysis.

The results of these studies are provided in Table 4 and show that compound II, which inhibits lysosomal fucosidase in cells, is toxic to a number of tumor cell lines, including colon and prostate cell lines. The results also demonstrate that compound II induces growth arrest in some normal (non-tumor) primary lines, but does not kill them.

TABLE 4

| Tissue | Type | Cell line | Cytotoxic EC50 (µM) | G1/S arrest (µM) | Primary effect |
| --- | --- | --- | --- | --- | --- |
| Connective | sarcoma | HT-1080 | 21 | 78 | apoptosis |
| Lung | carcinoma | A549 | 29 | 21 | apoptosis |
| Colon | carcinoma | HT-29 | 31 | none | apoptosis |
| Brain | blastoma | U-87 MG | 34 | 26 | growth arrest |
| Pancreas | carcinoma | BxPC-3 | 43 | 55 | growth arrest |
| Liver | carcinoma | HepG2 | 44 | 36 | apoptosis |
| Breast | carcinoma | MDA-MB-231 | 44 | none | |
| Cervix | carcinoma | HeLa | 47 | 70 | |
| Prostate | carcinoma | LNCaP | 54 | none | apoptosis |
| Blood | leukemia | K562 | 98 | 93 | growth arrest |
| Liver | carcinoma | SNU-423 | >100 | none | growth arrest |
| Ovary | carcinoma | SKOV3 | >100 | 98 | growth arrest |
| Mesenchymal stem | normal | HUMSC | 9 | 10 | growth arrest |
| Endothelium | normal | HUVEC | 14 | 14 | growth arrest |
| Skin | normal | NHDF | 22 | 14 | growth arrest |
| Renal | normal | HRPTEpiC | 72 | 10 | growth arrest |
| Primary hepatocyte | normal | HPH | >100 | — | no effect |

Example 6

Pharmacokinetics and Biodistribution of Compound II

To assess the pharmacokinetics of compound II (see Example 2) in mouse plasma, compound II was administered intravenously at a dosage of 1 mg/kg. Compound II concentration was measured at various time points up to 24 hours after administration, and the results are provided in Table 5.

TABLE 5

| Group ID | Animal ID | Treatment | Vehicle | Route | Regimen | Time (h) | Conc. of cmpd II (ng/ml) | Mean (ng/ml) |
|---|---|---|---|---|---|---|---|---|
| 1 | 1 | Compound II | PBS | IV | 1 mg/kg qdx1 | Pre-Dose | BQL | — |
| 1 | 2 | | | | | | BQL | |
| 1 | 3 | | | | | | BQL | |
| 1 | 1 | Compound II | PBS | IV | 1 mg/kg qdx1 | 0.0833 | 259 | 273 |
| 1 | 2 | | | | | | 247 | |
| 1 | 3 | | | | | | 313 | |
| 1 | 1 | Compound II | PBS | IV | 1 mg/kg qdx1 | 1 | 28.7 | 31.6 |
| 1 | 2 | | | | | | 31.8 | |
| 1 | 3 | | | | | | 34.3 | |
| 1 | 4 | Compound II | PBS | IV | 1 mg/kg qdx1 | 2 | 8.58 | 7.84 |
| 1 | 5 | | | | | | 5.83 | |
| 1 | 6 | | | | | | 9.10 | |
| 1 | 4 | Compound II | PBS | IV | 1 mg/kg qdx1 | 4 | 2.76 | 2.66 |
| 1 | 5 | | | | | | 1.86 | |
| 1 | 6 | | | | | | 3.36 | |
| 1 | 4 | Compound II | PBS | IV | 1 mg/kg qdx1 | 8 | 1.56 | 1.43 |
| 1 | 5 | | | | | | 1.17 | |
| 1 | 6 | | | | | | 1.57 | |
| 2 | 7 | Compound II | PBS | IV | 1 mg/kg qdx1 | 12 | 1.04 | 1.38 |
| 2 | 8 | | | | | | 1.06 | |
| 2 | 9 | | | | | | 2.04 | |
| 2 | 10 | Compound II | PBS | IV | 1 mg/kg qdx1 | 24 | BQL | — |
| 2 | 11 | | | | | | BQL | |
| 2 | 12 | | | | | | BQL | |

BQL = Below Quantitation limit <1.0 ng/ml
— = Not Applicable

To assess the biodistribution of compound II (see Example 2) in mouse liver and colon, compound II was administered intravenously at a dosage of 1 mg/kg. Compound II concentration was measured at 1 and 8 hours after administration, and the results are provided in Tables 6 and 7.

TABLE 6

Concentration of compound II in liver

| Group ID | Animal ID | Treatment | Vehicle | Route | Regimen | Time (h) | Conc. of cmpd II (ng/g) | Mean (ng/g) |
|---|---|---|---|---|---|---|---|---|
| 1 | 1 | Compound II | PBS | IV | 1 mg/kg qdx1 | 1 | 188 | 262 |
| 1 | 2 | | | | | | 298 | |
| 1 | 3 | | | | | | 301 | |
| 1 | 4 | Compound II | PBS | IV | 1 mg/kg qdx1 | 8 | 9.03 | 9.86 |
| 1 | 5 | | | | | | 7.64 | |
| 1 | 6 | | | | | | 12.9 | |

TABLE 7

Concentration of compound II in colon

| Group ID | Animal ID | Treatment | Vehicle | Route | Regimen | Time (h) | Conc. of cmpd II (ng/g) | Mean (ng/g) |
|---|---|---|---|---|---|---|---|---|
| 1 | 1 | Compound II | PBS | IV | 1 mg/kg qdx1 | 1 | 1930 | 1780 |
| 1 | 2 | | | | | | 1770 | |
| 1 | 3 | | | | | | 1640 | |
| 1 | 4 | Compound II | PBS | IV | 1 mg/kg qdx1 | 8 | 638 | 600 |
| 1 | 5 | | | | | | 289 | |
| 1 | 6 | | | | | | 872 | |

These results demonstrate rapid clearance of fucosidase inhibitors from mouse plasma, but reflect distribution of compound to tissue, particularly colon.

Example 7

In Vivo Efficacy in an Orthotopic Model of Human Hepatocellular Carcinoma

To assess the compounds in vivo, an orthotopic model of human hepatocellular carcinoma was used. The orthotopic tumor model was generated by implanting human hepatocarcinoma cell line HepG2 into nude mice and allowing the tumor cells to grow in vivo.

The efficacy study was carried out using 10 mice per group and two dosage regimens. Compound II (see Example 2) was administered by oral gavage (po) at a dosage of 175 mg/kg once daily for 3 weeks (QD×21) or at a dosage of 87.5 mg/kg twice daily for 3 weeks (BID×21). Vehicle (100 µL) was administered to control animals.

The animals were then assessed for changes in body weight and tumor volume, and the results are provided in Tables 8 and 9.

TABLE 8

Tumor Volume (mm$^3$)

| Dose (mg/kg) | Day 0 | Day 2 | Day 5 | Day 9 | Day 12 | Day 16 | Day 20 |
| --- | --- | --- | --- | --- | --- | --- | --- |
| 0 | 212 | 245 | 276 | 333 | 377 | 443 | 483 |
| 87.5 | 212 | 224 | 227 | 247 | 270 | 326 | 320 |
| 175 | 211 | 238 | 277 | 320 | 348 | 364 | 416 |

TABLE 9

Body Weight (g)

| Dose (mg/kg) | Day 0 | Day 2 | Day 5 | Day 9 | Day 12 | Day 16 | Day 20 |
| --- | --- | --- | --- | --- | --- | --- | --- |
| 0 | 22.23 | 22.35 | 21.97 | 21.74 | 22.2 | 20.63 | 20.4 |
| 87.5 | 22.45 | 22.05 | 21.93 | 21.58 | 21.51 | 20.39 | 20.86 |
| 175 | 22.93 | 22.94 | 22.28 | 22.1 | 22.26 | 20.58 | 19.98 |

Compound II demonstrated efficient reduction in tumor volume in the animal model for both dosing regimens, with greater reduction observed for the 87.5 mg/kg twice-daily dose. These data support the suitability of fucosidase inhibitors for targeting tumor cells in humans suffering from hepatocarcinoma or other liver conditions.

Example 8

Characterization of Compounds

In addition to the Examples above, the activity of the compounds herein may be measured by other assays known in the field, including but not limited to those described below.

Biochemical Efficacy in HepG2 Cells:

HepG2 cells, originally derived from an HCC tumor, produce hyperfucosylated glycoproteins. To assess the biochemical efficacy of compounds in hepatocytes, HepG2 cells are cultured using standard conditions and incubated in multi-well plates with buffer alone, one or more known fucosidase inhibitors, or test compounds. Following overnight incubation, cells are rinsed with cold PBS and lysed by freeze-thaw into 50 mM sodium citrate pH 4.8. Cell lysates are clarified by centrifugation and fucosidase activity assayed using 4-methylumbelliferyl-alpha-L-fucose assay (Available from Sigma-Aldrich, reference PMID 2137330) according to the manufacturer protocol. β-glucuronidase levels are also assayed using standard procedures in order to normalize for cell number and lysosomal function.

Functional Efficacy Studies in HepG2 Cells:

HepG2 cells are seeded at 1×10$^5$ cells per well in 12-well plates and allowed to recover for 24 hours. Cells are then incubated with test compounds for 72 hours. Cell status is then assessed by MTT proliferation assay.

It is expected that inhibition of fucosidase activity in the HepG2 cells will cause an accumulation of fucosylated proteins in the cells, leading to cell death or at least a slowing or stopping of cell proliferation.

Functional Efficacy in an Orthotopic Tumor Xenograft Model:

The efficacy of the compound is assayed in an orthotopic intrahepatic xenograft model as previously described (Ong, L. C. et al., Mol. Imaging Biol. 11:334-42 (2009); Aihara, A. et al., J. Hepatol. 52:63-71 (2010)). Briefly, 6-8 week severe combined immunodeficient (SCID) mice are anesthetized with an appropriate anesthetic, e.g., ketamine, diazepam or a combination thereof, and an upper midline laprotomy performed to expose the portal vein of the mouse through a midline incision of the abdomen. A suspension of 10$^6$ HepG2 cells is then injected into the portal vein over the course of one minute using a 30-gauge needle. The incision is then sutured closed and the animals kept warm until fully awake.

To measure the efficacy of compound treatment, positron emission tomography (PET) using an appropriate radiolabeled agent, such as 2-deoxy-2-(F-18)-fluoro-D-glucose ($^{18}$F-FDG), is carried out (Ong, L. C. et al., Mol. Imaging Biol. 11:334-42 (2009)) to follow the progression of the HepG2 induced tumor in treated and control mice via a non-invasive method. The efficacy of compound treatment is also measured in vivo by histological analysis of the tumor area in treated and control animals.

Measurement of lysosomal storage disease indicators, including glycosaminoglycan (GAG) levels in the lysosome, urine and blood, are also assayed in the orthotopic tumor model.

It is expected that administration of the compound will decrease tumor size or slow the progression of tumor growth compared to subjects not receiving the compound. It is also expected that administration of the compound will increase the level of fucosylated proteins in the lysosomes of cells taking up the compound, as measured by GAG assays.

Example 9

Characterization of Compounds

In addition to the Examples above, the in vivo activity of the compounds herein may be measured by other animal models known in the field, including but not limited to those described below.

Functional Efficacy in a Subcutaneous Tumor Xenograft Model:

The efficacy of the compound is assayed in a subcutaneous xenograft model. Suitable subcutaneous xenograft models can be obtained using 6-8 week severe combined immunodeficient (SCID) mice by anesthetizing with an appropriate anesthetic, e.g., ketamine, diazepam or a combination thereof, and then injecting with an appropriate suspension of cells, such as Huh-7, SK-Hep1, HA22T/VGH, or PLC/PRF/5 cells for hepatocellular carcinoma; BT-474, MDA-MB-453, MCF-7, or MDA-MB-231 cells for breast cancer; NCI-H460, A549, NCI-1703, or NCI-H226 cells for lung cancer; SNU-1, NCI-N87, TMC-1, TSGH, or TSGH-53 cells for gastric cancer; MV4-11, RS4-11, or MOLM-13 cells for acute myeloid leukemia; COLO 205 or HT-29 cells for colon cancer; RPMI2650 cells for nasal carcinoma; PANC1 or MIA-PaCa 2 cells for pancreatic carcinoma; RPMI-2650, Detroit 562, FaDu, or HSC-3 cells for head and neck cancer; and TT cells for thyroid carcinoma. The incision is then sutured closed and the animals kept warm until fully awake.

To measure the efficacy of compound treatment, positron emission tomography (PET) using an appropriate radiolabeled agent, such as 2-deoxy-2-(F-18)-fluoro-D-glucose ($^{18}$F-FDG), is carried out (Ong, L. C. et al., Mol. Imaging Biol. 11:334-42 (2009)) to follow the progression of the induced tumor in treated and control mice via a non-invasive method. The efficacy of compound treatment is also measured in vivo by histological analysis of the tumor area in treated and control animals.

Measurement of lysosomal storage disease indicators, including glycosaminoglycan (GAG) levels in the lysosome, urine and blood, are also assayed in the subcutaneous tumor model.

It is expected that administration of the compound will decrease tumor size or slow the progression of tumor growth compared to subjects not receiving the compound. It is also expected that administration of the compound will increase the level of fucosylated proteins in the lysosomes of cells taking up the compound, as measured by GAG assays.

Functional Efficacy in an Orthotopic Tumor Xeno Graft Model:

The efficacy of the compound is assayed in an orthotopic xenograft model. Suitable orthotopic xenograft models can be obtained using 6-8 week severe combined immunodeficient (SCID) mice by anesthetizing with an appropriate anesthetic, e.g., ketamine, diazepam or a combination thereof, and then injecting with an appropriate suspension of cells, such as Huh-7, PLC/PRF/5, or BNL 1ME A.7R.1-luc cells for hepatocellular carcinoma; patient-derived cells from, for example, hepatocellular carcinoma patients for patient-derived xenograft (PDX) models; Detroit 562 or HSC-3 cells for head and neck cancer; and B16-F10 cells for melanoma. The incision is then sutured closed and the animals kept warm until fully awake.

Additionally, a spontaneous lymph mode metastasis model of melanoma can be obtained by inoculating B16-F10-luc2 murine melanoma cells in the hind foot pad of immune-competent syngeneic C57B1/6 mice.

To measure the efficacy of compound treatment, positron emission tomography (PET) using an appropriate radiolabeled agent, such as 2-deoxy-2-(F-18)-fluoro-D-glucose ($^{18}$F-FDG), is carried out (Ong, L. C. et al., Mol. Imaging Biol. 11:334-42 (2009)) to follow the progression of the induced tumor in treated and control mice via a non-invasive method. The efficacy of compound treatment is also measured in vivo by histological analysis of the tumor area in treated and control animals.

Measurement of lysosomal storage disease indicators, including glycosaminoglycan (GAG) levels in the lysosome, urine and blood, are also assayed in the subcutaneous tumor model.

It is expected that administration of the compound will decrease tumor size or slow the progression of tumor growth compared to subjects not receiving the compound. It is also expected that administration of the compound will increase the level of fucosylated proteins in the lysosomes of cells taking up the compound, as measured by GAG assays.

Example 10

Administration of Compounds In Vivo

HCC is the 5th most common malignant tumor to be diagnosed, and worldwide accounts for nearly 500,000 deaths annually. Surgical removal, transplant and physical destruction of tumor tissue are first choices for treatment, but only 5 to 10% of patients present with tumors suitable for these approaches (Ribero, D. et al., Expert Rev. Anticancer Ther. 6:567-579 (2006); Lau, W. Y. et al., J. Am. Coll. Surg. 202:155-168 (2006); Lin, X. D. et al., Hepatobiliary Pancreat. Dis. Int. 5:16-21 (2006)). Further, systemic chemotherapy yields low response rates of 15-20%, both because of the toxicity of chemotherapeutics and tumor cell resistance (Chan, J. Y., et al., Life Sci. 67:2117-2124 (2000); Plosker, G. L., et al., Drugs 45:788-856 (1993)).

For example, doxorubicin is a cancer chemotherapeutic with high efficiency against a wide variety of tumors, and is especially toxic to cells undergoing rapid growth, including tumor cells. However, the use of doxorubicin in the treatment of hepatocellular carcinoma is limited by significant liver and heart toxicity and suppression of blood-cell production (Danesi, R., et al., Clin. Pharmacokinet. 41:431-444 (2002)). In addition, hepatocellular carcinoma cells show high rates of conversion to drug-resistant types (Hu, Y., et al., Int. J. Oncol. 25:1357-1364 (2004)).

An alternative approach to therapy utilizes radiation. For example, a new treatment for liver cancer that is currently being tested involves injecting microscopic glass beads that have been labeled with a radioactive material ($^{90}$Y) into the main liver artery, from where it passes in to the small blood vessels that perfuse tumor tissue. The radiation then destroys the tumor tissue. However, significant shunting of blood from the hepatic artery to the lungs precludes use of the glass beads in many patients. Significant reflux of beads into arteries feeding the gastrointestinal tract can also cause serious side-effects. Effective delivery of therapy to tumor tissue therefore requires a more directed approach that does not rely on large materials that will be trapped in blood vessels.

In order to assess the compounds in vivo, orthotopic models of human hepatocellular carcinoma are used.

To generate orthotopic tumors in animals, human hepatocarcinoma cell lines are implanted into nude mice, rats, or other appropriate animal and the tumor cells allowed to grow in vivo. HCC cell lines useful for orthotopic models include, but are not limited to, those cell lines described above, such as Hep3B, HepG2, SK-Hep1, HA22T/VGH, PLC/PRF/5, and Huh-7. Orthotopic tumor models of HCC are known in the art and are described in, for example, Okubo et al. (J Gastroenterol Hepatol. 2007 22:423-8); Armengol et al., (Clin Cancer Res. 2004 10:2150-7); and Yao et al., (Clin Cancer Res. 2003 9:2719-26).

To first establish a dose range for administration of the compounds and controls in vivo, a small dose range study is carried out using 5 mice per group, receiving compound (e.g., up to 200 mg/kg/day). The test agents are administered either intravenously or intraperitoneally daily for two weeks (QD×14) and the subject animals tested for change in body weight, any clinical observations, and clinical pathology and tissue histopathology at study endpoint.

To carry out an efficacy study, 8 to 10 mice per group are used, and 3 test dose ranges of the compounds above are administered to the animals receiving human HCC cells and control animals. Test agents are administered either intravenously or intraperitoneally and are administered at an appropriate frequency, e.g., daily for 4 weeks (QD×28), daily for 3 weeks (QD×21) or daily for 2 weeks (QD×14). Subject animals are then assessed for any changes in body weight, clinical observations, and in vivo efficacy measurements, such as tumor volume, liver histopathology, and general clinical pathology, using techniques known in the art.

The ability of the compounds to reduce growth of hepatocellular carcinoma cells in vivo demonstrates that compounds are being effectively delivered into liver cells resulting in a biologically measurable effect. Demonstration of efficient tumor death in animal models suggests that compounds are effective at targeting tumor cells in humans suffering from hepatocarcinoma or other liver conditions.

Another relevant animal model for hepatocellular carcinoma (HCC) for testing biodistribution and efficacy of therapeutics is the woodchuck hepatitis virus (WHV)-infected Eastern woodchuck (Tennant, B. C., et al., Gastroenterology 127:S283-293 (2004)). Nearly all woodchucks neonatally infected with the virus develop HCC within a median interval of 24 months. Median life expectancy is 30 months, however WHV-infected woodchucks do not develop cirrhosis, a condition present in the majority of HCC patients. Woodchuck hepatitis virus and human hepatitis B virus are similar in structure, genetics, methods of transmission, course of infection and progression to hepatocellular carcinoma. There are significant similarities that underscore the importance of this model. Similar to humans, more than half of all woodchucks exposed to hepatitis virus shortly after birth develop a chronic infection and nearly all chronically infected woodchucks develop hepatocellular carcinoma approximately 20 to 28 months after exposure. The remaining inoculated neonatal woodchucks often develop acute hepatitis, but will develop antibodies to the virus and recover. Between 17 and 25% of these "recovered" animals develop HCC between 29 to 56 months after exposure. Development of HCC after apparently recovering from hepatitis infection is also seen in humans.

To determine the effectiveness of compounds on liver tumor cells, uptake and toxicity of control and test compounds are studied in the woodchuck HCC model. In one embodiment, six chronically infected woodchucks and four uninfected woodchucks, approximately 1.5-2 years old are used.

A useful compound will generally exhibit the following characteristics: 1) does not adversely affect the already compromised function of the liver, 2) measurable uptake by the liver and malignant liver tissue, 3) and upon uptake, is toxic to tumor cells and causes tumor regression.

Measurement of lysosomal storage disease indicators, including oligosaccharide levels in the lysosome, urine and blood, are also assayed in the tumor models.

Numerous modifications and variations in the invention as set forth in the above illustrative examples are expected to occur to those skilled in the art. Consequently only such limitations as appear in the appended claims should be placed on the invention.

What is claimed:

1. A compound of formula I:

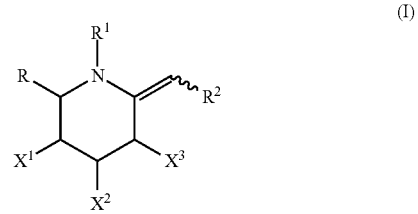

wherein:

$X^1$, $X^2$, and $X^3$ are independently selected from the group consisting of OH, halo, and $O(C)OCH_3$;

R is selected from the group consisting of $C_{1-3}$alkyl and $C_{1-3}$haloalkyl;

$R^1$ is selected from the group consisting of H, $C_{1-3}$alkyl, OH, —$CO_2C_{1-3}$alkyl;

$R^2$ is selected from the group consisting of —$NR^bC(O)R^a$, —$NR^bC(O)OR^a$, —$NR^bC(O)NR^cR^a$, —$NR^bC(O)SR^a$, —$C(O)R^a$, and —$C(O)NR^bR^a$;

$R^a$ is —$C_{0-3}$alkylene-G;

G is selected from the group consisting of aryl, heteroaryl, cycloalkyl, and heterocycloalkyl; and $R^b$ and $R^c$ are independently selected from the group consisting of H and $C_{1-3}$alkyl.

2. The compound of claim 1, wherein $X^1$, $X^2$, and $X^3$ are OH, R is methyl, and/or $R^1$ is H.

3. The compound of claim 1, wherein $R^2$ is —$NR^bC(O)R^a$ or —$C(O)NR^bR^a$.

4. The compound of claim 1, wherein G is selected from the group consisting of optionally substituted indolyl, benzothiophenyl, fluorenyl, indenyl, dihydro indenyl, and phenyl.

5. The compound of claim 1, wherein G is selected from the group consisting of optionally substituted phenyl and

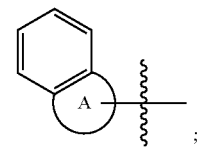

wherein A is a 5-, 6-, 7-, 8-, 9-, or 10-membered carbocyclic or heterocyclic ring system.

6. The compound of claim 1, wherein G is selected from the group consisting of

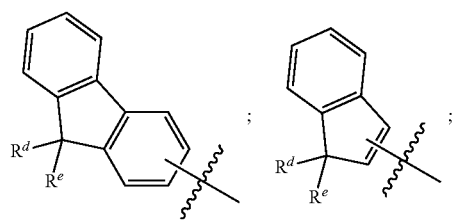

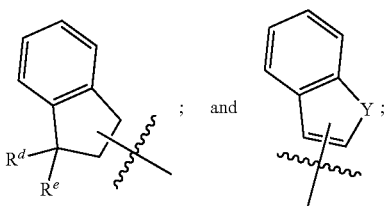

$R^d$ and $R^e$ are independently selected from the group consisting of H, $OR^f$, $NR^fR^g$, $C_{1-3}$alkyl, and $C_{1-5}$cycloalkyl; or $R^d$ and $R^e$ taken together with the carbon atom to which they are attached form C=O;

$R^f$ and $R^g$ are independently selected from the group consisting of H and $C_{1-3}$alkyl; and Y is selected from the group consisting of NH, N—$C_{1-3}$alkyl, S, SO, $SO_2$, and O.

7. The compound of claim 1, wherein G is selected from the group consisting of

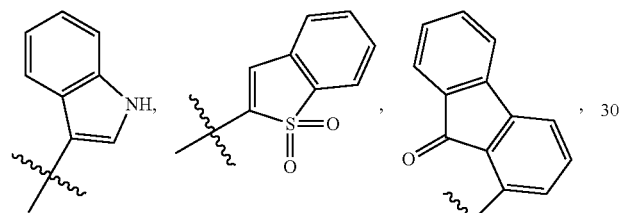

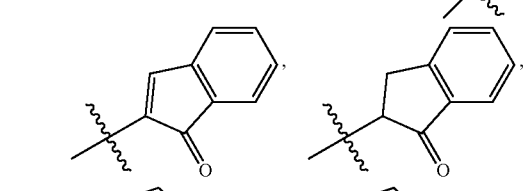

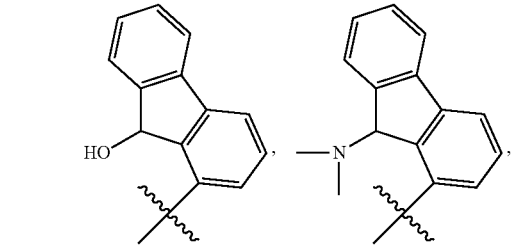

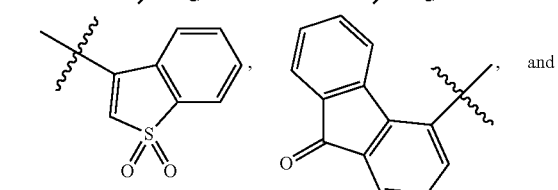

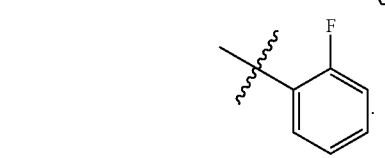

8. The compound of claim 1, wherein $R^a$ is selected from the group consisting of

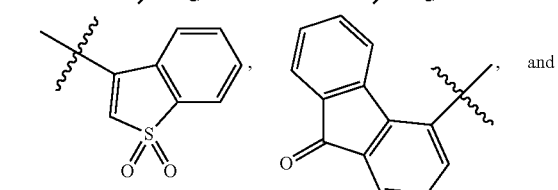

9. The compound of claim 1, wherein the compound of formula I has the following structure:

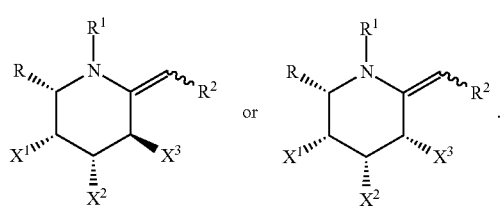

.

10. The compound of claim 1, wherein the compound is selected from the group consisting of:

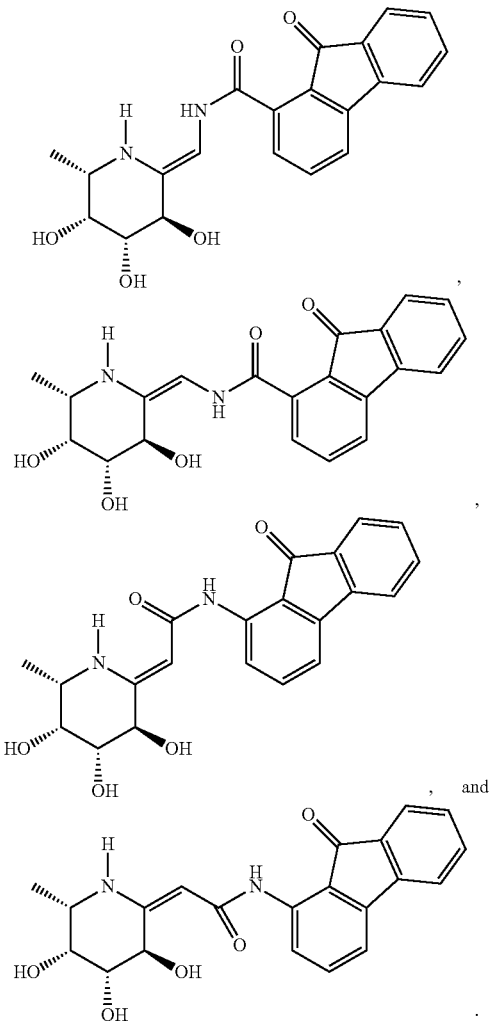

, and

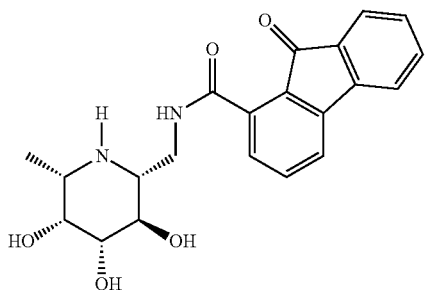

11. A method for treating a tumor or cancer in a subject in need thereof comprising administering the compound of claim 1, compound II, or compound III, in a therapeutically effective amount:

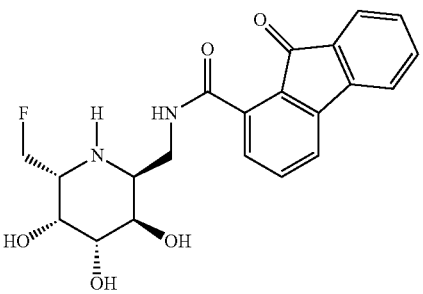

wherein the tumor or cancer is liver cancer, breast cancer, melanoma, lung cancer, leukemia, pancreatic cancer, gastric cancer, colorectal cancer, and head and neck cancer.

12. The method of claim 11, wherein the compound reduces tumor metastasis in a subject, the treatment results in a decrease in tumor size in the subject, and/or the treatment results in a reduction of alpha-fetoprotein levels in blood of the subject compared to levels before treatment.

13. The method of claim 11, wherein the tumor is a result of hepatocellular carcinoma, hepatitis virus infection, cirrhosis, toxic liver damage, and hereditary hemochromatosis.

14. The method of claim 11, wherein the compound is administered intravenously.

15. The method of claim 11, wherein the compound is administered in combination with a second agent.

16. The method of claim 15, wherein the second agent is a chemotherapeutic agent selected from the group consisting of doxorubicin and 5-fluorouracil.

17. The method of claim 15, wherein the second agent is a cytotoxic agent.

18. The method of claim 15, wherein the second agent is a radioisotope.

19. The method of claim 15, wherein the tumor is associated with hepatitis virus infection, and the second agent is an antiviral agent.

20. The method of claim 14, wherein the compound is administered via the hepatic artery.

21. The method of claim 15, wherein the second agent is selected from the group consisting of a chemotherapeutic agent, a cytotoxic agent, a radioisotope, an anti-viral agent, an anti-fungal agent, an anti-inflammatory agent and an antibody.

22. The method of claim 17, wherein the cytotoxic agent is selected from the group consisting of mechlorethamine hydrochloride, cyclophosphamide, ifosfamide, chlorambucil, melphalan, busulfan, thiotepa, carmustine, lomustine, dacarbazine and streptozocin.

23. The method of claim 18, wherein the radioisotope is selected from the group consisting of $^{131}I$, $^{125}I$, $^{111}In$, $^{90}Y$, $^{67}Cu$, $^{127}Lu$, $^{212}Bi$, $^{213}Bi$, $^{255}Fm$, $^{149}Tb$, $^{223}Rd$, $^{213}Pb$, $^{212}Pb$, $^{211}At$, $^{89}Sr$, $^{153}Sm$, $^{166}Ho$, $^{225}Ac$, $^{186}Re$, $^{67}Ga$, $^{68}Ga$ and $^{99m}Tc$.

24. A pharmaceutical composition comprising the compound of claim 1 and a pharmaceutically acceptable carrier.

* * * * *